(12) United States Patent
Mueller et al.

(10) Patent No.: US 10,188,560 B2
(45) Date of Patent: Jan. 29, 2019

(54) ABSORBENT ARTICLE HAVING FINGER TABS AND METHODS OF MANUFACTURING SAME

(71) Applicant: KIMBERLY-CLARK WORLDWIDE, INC., Neenah, WI (US)

(72) Inventors: Justin M. Mueller, Oshkosh, WI (US); Blake A. Hondl, Neenah, WI (US); William J. Meyer, Appleton, WI (US); Brian K. Rhodes, Winneconne, WI (US); Sarah A. Kleuskens, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 15/327,496

(22) PCT Filed: Nov. 26, 2014

(86) PCT No.: PCT/US2014/067615
§ 371 (c)(1),
(2) Date: Jan. 19, 2017

(87) PCT Pub. No.: WO2016/085491
PCT Pub. Date: Jun. 2, 2016

(65) Prior Publication Data
US 2017/0252230 A1    Sep. 7, 2017

(51) Int. Cl.
*A61F 13/49* (2006.01)
*A61F 13/56* (2006.01)
(Continued)

(52) U.S. Cl.
CPC .... *A61F 13/4963* (2013.01); *A61F 13/15585* (2013.01); *A61F 13/15699* (2013.01);
(Continued)

(58) Field of Classification Search
CPC .......... A61F 13/15699; A61F 13/15739; A61F 13/1574; A61F 13/15756; A61F 13/496;
(Continued)

(56) References Cited

U.S. PATENT DOCUMENTS 5,136,932 A * 8/1992 Giamello .............. F01B 1/0689
91/497
5,163,932 A * 11/1992 Nomura ............ A61F 13/49009
2/401
(Continued)

FOREIGN PATENT DOCUMENTS

CN    101272754 A    9/2008
WO    2011064681 A2    6/2011

OTHER PUBLICATIONS

International Search Report and Written Opinion of International Application No. PCT/US2014/067615, dated Jul. 27, 2015, 16 pages.
(Continued)

*Primary Examiner* — Lynne Anderson
(74) *Attorney, Agent, or Firm* — Armstrong Teasdale LLP

(57) ABSTRACT

A method of manufacturing an absorbent article includes feeding a first web of material in a machine direction, feeding a second web of material in the machine direction, the second web being spaced from the first web by a gap, attaching an absorbent assembly to the first web and the second web such that the absorbent assembly spans the gap between the first and second webs, forming a partial cut line through the second web, folding the first web into face-to-face relationship with the second web after forming the partial cut line, and cutting the first and second webs after folding the first web into face-to-face relationship with the second web to separate the absorbent article from the first
(Continued)

and second webs. The partial cut line defines at least one finger tab on the absorbent article.

20 Claims, 10 Drawing Sheets

(51) Int. Cl.
*A61F 13/496* (2006.01)
*A61F 13/66* (2006.01)
*A61F 13/15* (2006.01)

(52) U.S. Cl.
CPC .. *A61F 13/15723* (2013.01); *A61F 13/15739* (2013.01); *A61F 13/15756* (2013.01); *A61F 13/15764* (2013.01); *A61F 13/565* (2013.01); *A61F 13/665* (2013.01); *A61F 2013/49065* (2013.01); *A61F 2013/49087* (2013.01)

(58) Field of Classification Search
CPC ............. A61F 13/4963; A61F 13/5644; A61F 13/565; A61F 2013/49063; A61F 2013/49065; A61F 2013/49066; A61F 2013/49081; A61F 2013/49096
See application file for complete search history.

(56) References Cited

U.S. PATENT DOCUMENTS

| | | | |
|---|---|---|---|
| D428,143 S | 7/2000 | Schmoker et al. | |
| D428,145 S | 7/2000 | Bruemmer-Prestley et al. | |
| 6,352,528 B1 | 3/2002 | Weber et al. | |
| 6,976,978 B2* | 12/2005 | Ruman | A61F 13/15756 604/385.01 |
| 7,765,614 B2* | 8/2010 | Takino | A61F 13/496 2/111 |
| 7,887,522 B2* | 2/2011 | Roe | A61F 13/496 604/385.01 |
| 7,985,210 B2* | 7/2011 | Ashton | A61F 13/493 604/317 |
| 8,066,687 B2 | 11/2011 | Ashton et al. | |
| 8,337,479 B2* | 12/2012 | Nilsson | A61F 13/15756 604/387 |
| 8,545,474 B2 | 10/2013 | Schlipp et al. | |
| 8,663,184 B2* | 3/2014 | Liu | A61F 13/496 604/386 |
| 8,936,586 B2* | 1/2015 | Roe | A61F 13/49 604/385.14 |
| 2003/0055389 A1 | 3/2003 | Sanders et al. | |
| 2006/0149208 A1 | 7/2006 | Carr | |
| 2008/0249493 A1* | 10/2008 | Kobayashi | A61F 13/15756 604/378 |
| 2012/0101468 A1 | 4/2012 | Sperl | |
| 2012/0253310 A1* | 10/2012 | Hahn | A61F 13/494 604/385.3 |
| 2012/0259307 A1* | 10/2012 | Otsubo | A61F 13/49011 604/385.29 |
| 2012/0283683 A1* | 11/2012 | Tai | A61F 13/49011 604/385.3 |
| 2013/0165898 A1 | 6/2013 | Rhodes et al. | |
| 2014/0135730 A1 | 5/2014 | Mlinar et al. | |
| 2014/0257227 A1 | 9/2014 | Roe | |

OTHER PUBLICATIONS

International Preliminary Report of Patentability of International Application No. PCT/US2014/067615, dated Nov. 30, 2016, 3 pages.
Extended European Search Report for EP Patent Application No. 14906886.8, dated May 7, 2018, 9 pages.

* cited by examiner

ABSORBENT ARTICLE HAVING FINGER TABS AND METHODS OF MANUFACTURING SAME

FIELD

The field of the disclosure relates generally to absorbent articles intended for personal wear, and more specifically to absorbent articles having finger tabs and methods of manufacturing such articles.

BACKGROUND

Absorbent articles, such as diapers, incontinence garments, training pants, and the like are well known in the art. These articles, which are often disposable, are capable of absorbing and retaining fluids and other bodily discharges. Some absorbent articles are designed to look and feel like conventional underpants for a variety of reasons, such as to promote an improved sense of normalcy (in the case of incontinence garments) or to incentivize a child who is in the toilet training process.

Some absorbent articles, such as incontinence garments and toilet training pants, come pre-assembled in a wear configuration to more closely resemble conventional underpants. In particular, front and back waist regions of such training pants are typically attached at a seam (either permanently or refastenably) to define a wear configuration of the pant having a waist opening and leg openings. Such seams may be configured for selective, manual separation to enable a donned absorbent article to be removed without having to remove the wearer's clothing or shoes.

Some users may find the attachment difficult to open because the attachment is designed to withstand stresses placed on the attachment by movement of the wearer without unintentionally opening (i.e., separation of the seam). Accordingly, some absorbent articles include a finger tab to assist users in opening the attachment.

In some absorbent articles, finger tabs are formed separately from and attached to the article during the manufacturing process. Manufacturing such articles, however, requires additional, complicated processing steps (e.g., forming the finger tabs, registering the finger tabs with a moving web or article, and attaching the finger tabs to the moving web or article) as compared to articles without finger tabs. As a result, certain absorbent articles, such as articles manufactured in a cross-machine direction (i.e., processes in which the longitudinal direction of the article is oriented perpendicular to the conveying direction of the process), lack satisfactory means of separating the seams of the article.

Thus, there exists a need for an absorbent article having finger tabs that facilitate separating the seams of the article. Moreover, there exists a need for a simplified process for manufacturing such articles that does not require complicated processing steps.

BRIEF DESCRIPTION

In one aspect, a method of manufacturing an absorbent article is provided. The method includes feeding a first web of material in a machine direction, feeding a second web of material in the machine direction, the second web being spaced from the first web by a gap, attaching an absorbent assembly to the first web and the second web such that the absorbent assembly spans the gap between the first and second webs, forming a partial cut line through the second web, folding the first web into face-to-face relationship with the second web after forming the partial cut line, and cutting the first and second webs after folding the first web into face-to-face relationship with the second web to separate the absorbent article from the first and second webs. The partial cut line defines at least one finger tab on the absorbent article.

In another aspect, a method of manufacturing an absorbent article is provided. The method includes feeding a first web of material in a machine direction, feeding a second web of material in the machine direction, the second web being spaced from the first web by a gap, attaching an absorbent assembly to the first web and the second web such that the absorbent assembly spans the gap between the first and second webs, folding the first web into face-to-face relationship with the second web, and cutting the first and second webs while the first and second webs are in face-to-face relationship to separate the absorbent article from the first and second webs, wherein cutting the first and second webs forms finger tabs on the absorbent article.

In yet another aspect, a method of manufacturing an absorbent article is provided. The method includes feeding a first web of material in a machine direction, feeding a second web of material in the machine direction, the second web being spaced from the first web by a gap, attaching an absorbent assembly to the first web and the second web such that the absorbent assembly spans the gap between the first and second webs, folding the first web into face-to-face relationship with the second web, and forming an undulated cut line through at least one of the first web and the second web to form an integral finger tab on the absorbent article.

In yet another aspect, an absorbent article is provided. The absorbent article defines a longitudinal direction and a transverse direction. The absorbent article includes a front panel, a rear panel, an absorbent assembly extending longitudinally between and interconnecting the front panel and the rear panel, and a gripping feature. The front panel defines a front waist edge and first and second front side edges spaced apart in the transverse direction. The rear panel defines a rear waist edge spaced apart from the first waist edge in the longitudinal direction, and first and second rear side edges spaced apart in the transverse direction. The front panel is connected to the rear panel by a pair of side seams when the absorbent article is in a wear configuration to define a waist opening and a pair of leg openings. Each side seam extends between one of the leg openings and the waist opening. The gripping feature includes a pair of finger tabs integrally formed with one of the front panel and the rear panel. The pair of finger tabs includes a first finger tab extending transversely outward from the front panel or rear panel along the first side edge of the corresponding front panel or rear panel, and a second finger tab extending transversely outward from the front panel or rear panel along the second side edge of the corresponding front panel or rear panel.

In yet another aspect, a method of manufacturing an absorbent article is provided. The method includes feeding a web of material in a machine direction, the web defining a first portion and a second portion spaced from the first portion in a cross-machine direction, attaching an absorbent assembly to the web such that the absorbent assembly is oriented in the cross-machine direction, forming a partial cut line through the first portion of the web, folding the first portion of the web into face-to-face relationship with the second portion of the web after forming the partial cut line, and cutting the web after folding the first portion into face-to-face relationship with the second portion to separate the absorbent article from the web, the partial cut line defining at least one finger tab on the absorbent article.

In yet another aspect, an absorbent article is provided. The absorbent article defines a longitudinal direction and a transverse direction. The absorbent article includes a chassis, an absorbent assembly, and a gripping feature. The chassis includes a front portion, a rear portion, and a crotch portion extending between and interconnecting the front portion and the rear portion. The front portion defines first and second front side edges spaced apart in the transverse direction, and the rear portion defines first and second rear side edges spaced apart in the transverse direction. The front portion is connected to the rear portion by a pair of side seams when the absorbent article is in a wear configuration to define a waist opening and a pair of leg openings. Each side seam extends between one of the leg openings and the waist opening. The absorbent assembly is attached to the chassis along at least the crotch portion. The gripping feature includes a pair of finger tabs integrally formed with one of the front portion and the rear portion of the chassis. The pair of finger tabs includes a first finger tab extending transversely outward from the front portion or rear portion along the first side edge of the corresponding front portion or rear portion, and a second finger tab extending transversely outward from the front portion or rear portion along the second side edge of the corresponding front portion or rear portion.

DETAILED DESCRIPTION OF THE DRAWINGS

Figure 1:
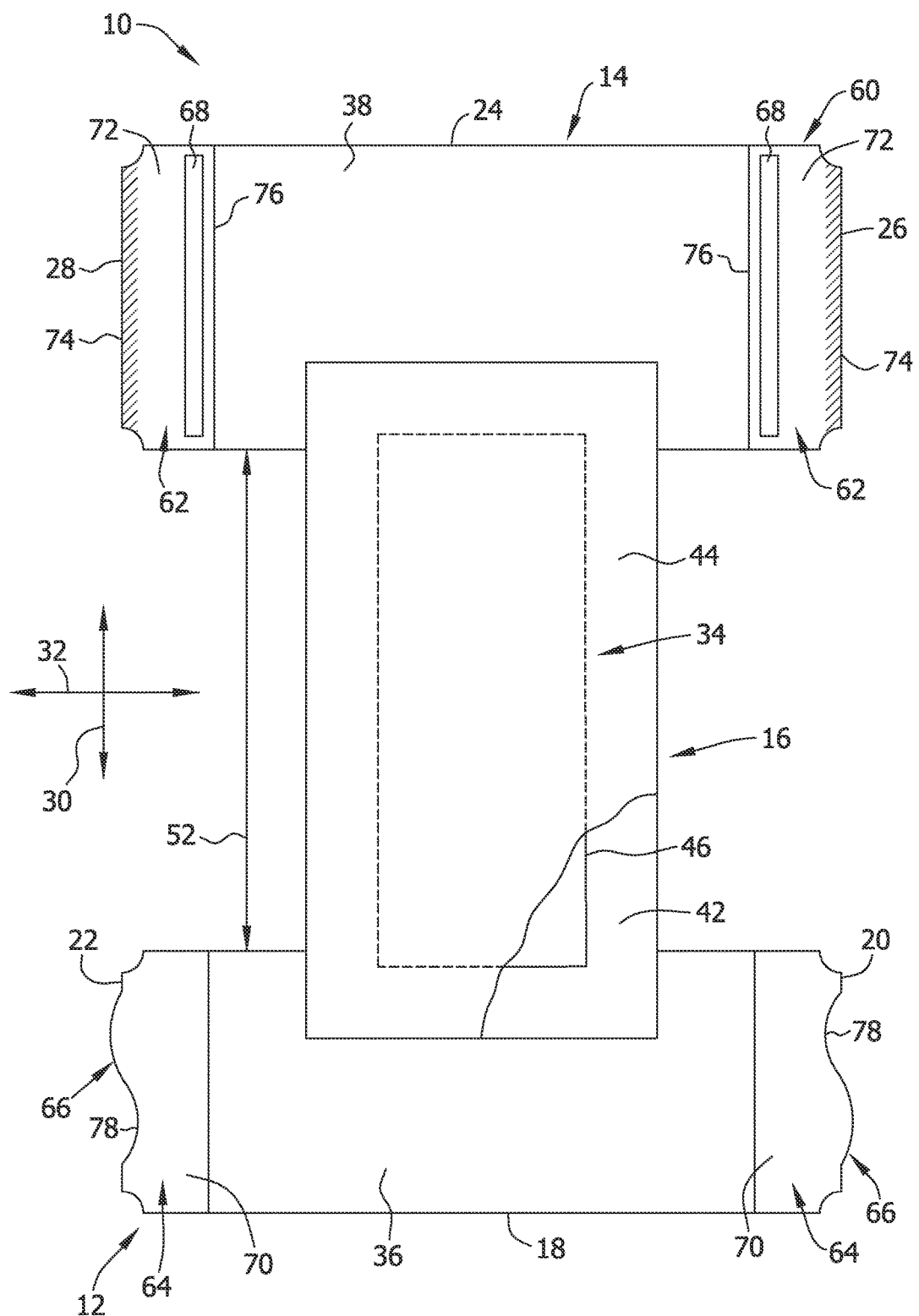
FIG. 1 is a top plan view of one suitable embodiment of an absorbent article according to the present disclosure in the form of a diaper pant, the diaper pant being illustrated in an open and laid flat condition to show an inner surface of the diaper pant that faces towards the wearer when the diaper pant is worn.
Figure 2:
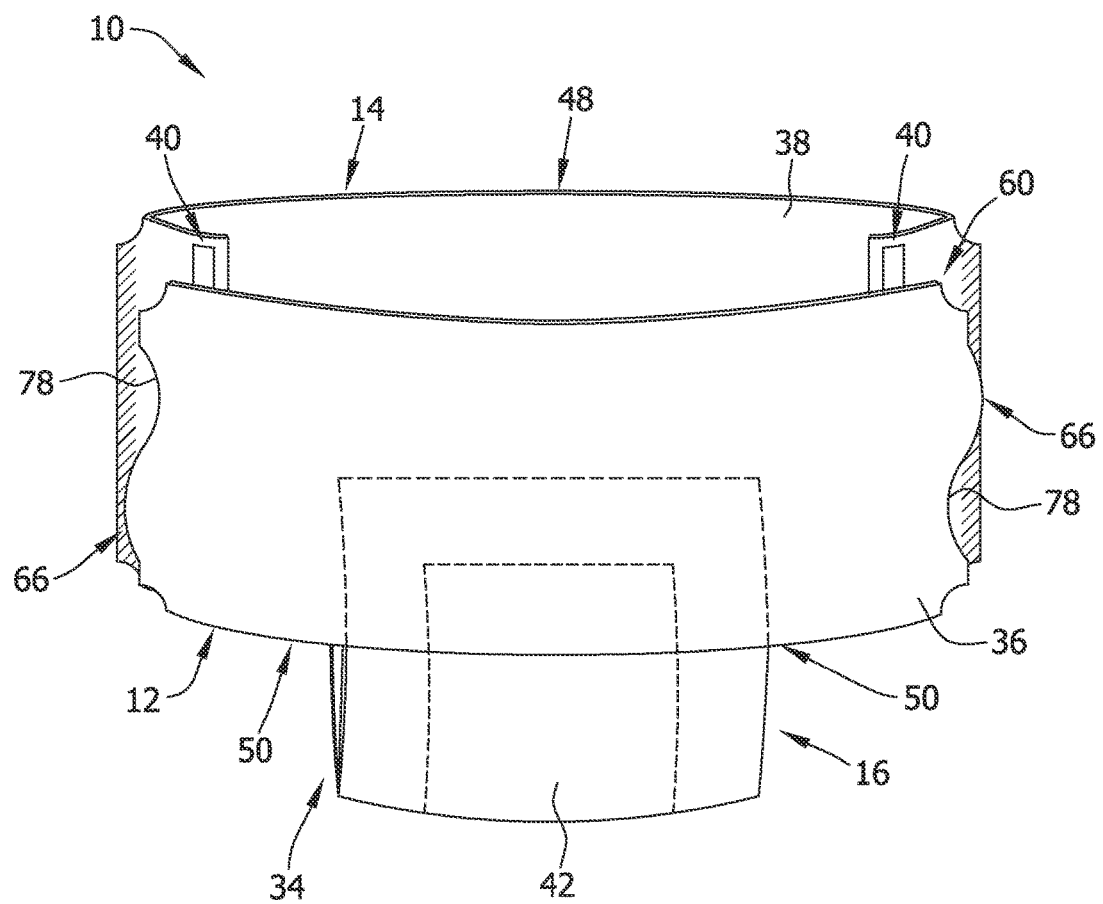
FIG. 2 is a front view of the diaper pant in a wear configuration.

With reference now to the drawings, FIGS. 1 and 2 illustrate one suitable embodiment of an absorbent article of the present disclosure in the form of a diaper pant, indicated generally at 10. While the present disclosure will be made in the context of the diaper pant 10, it should be understood that aspects of the present disclosure are applicable to other absorbent articles, such as, for example, refastenable diapers, adult incontinence garments, children's training pants, swim diapers, feminine care articles and the like.

In one suitable embodiment, the diaper pant 10 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper pant 10 (or more broadly, the absorbent article) can be reusable. That is, the absorbent article can be intended for multiple uses without departing from some aspects of this disclosure.

FIG. 1 illustrates the diaper pant 10 in an open and laid flat condition to show an inner surface of the diaper that faces the wearer when the diaper is worn. As seen therein, the diaper pant 10 has a longitudinal direction 30 and a transverse or lateral direction 32. In the longitudinal direction 30, the diaper pant 10 defines a front region 12, a rear region 14, and a crotch region 16 extending between and connecting the front region 12 and the rear region 14. The front region 12 of the diaper pant 10 is intended to be generally located on the front of a wearer during use; the rear region 14 is intended to be generally located at the back of the wearer during use; and the crotch region 16 is intended to be generally located between the legs of the wearer during use.

In the front region 12, the diaper pant 10 has a front waist edge 18 and transversely opposed first and second front side edges 20, 22. A rear waist edge 24 and transversely opposed first and second rear side edges 26, 28 are located in the rear region 14 of the diaper pant 10. In the illustrated embodiment, the front waist edge 18 and the rear waist edge 24 are straight edges. That is, the front waist edge 18 and the rear waist edge 24 are substantially free from curves, bends, angles, notches or irregularities. It is understood, however, that the front waist edge 18 and/or the rear waist edge 24 can be cut in any suitable shape as is known in the art (e.g., arcuate).

In the illustrated embodiment, the diaper pant 10 includes a central absorbent assembly, indicated generally at 34, that extends longitudinally from the front region 12 through the crotch region 16 to the rear region 14. The central absorbent assembly 34, of the illustrated embodiment, comprises an outer cover 42 and a bodyside liner 44 connected to the outer cover 42 in a superposed relation by suitable means such as adhesives, ultrasonic bonds, thermal bonds, pressure bonds, and combinations thereof. An absorbent structure 46 is disposed between the outer cover 42 and the bodyside liner 44. A portion of the bodyside liner 44 is shown cut away in FIG. 1 to reveal the underlying absorbent structure 46 and outer cover 42. In one suitable embodiment, edges of the bodyside liner 44 are wrapped around and secured to a bottom of the absorbent structure 46, and edges of the outer cover 42 are wrapped around the edges of the bodyside liner 44 and the absorbent structure 46, and are secured to a top of the absorbent structure 46. The absorbent structure 46 may also be wrapped or encompassed by a suitable core wrap (not shown) that aids in maintaining the integrity and shape of the absorbent structure.

In one suitable embodiment, the front and rear regions 12, 14 of the diaper pant 10 are constructed from separate front and rear panels 36, 38, respectively, that are interconnected via the absorbent assembly 34. That is, the front region 12 is formed from the front panel 36 and the rear region 14 is formed from the separate, rear panel 38. In other suitable embodiments, the front and rear regions 12, 14 of the diaper pant 10 may be constructed from a single, continuous sheet of material, such as a liquid impermeable material, having cutouts formed therein to define leg openings (see, e.g., FIGS. 8 and 9).

In the illustrated embodiment, each panel 36, 38 is attached to the outer cover 42 of the absorbent assembly 34 by suitable means such as adhesives, ultrasonic bonds, thermal bonds, pressure bonds, and combinations thereof. In other suitable embodiments, the panels 36, 38 may be joined to other portions of the central absorbent assembly 34, such as the bodyside liner 44. As seen in FIG. 1, the front panel 36 is spaced from the rear panel 38 to define a gap 52. The absorbent assembly 34 spans the gap 52 and connects the front panel 36 to the rear panel 38.

The diaper pant 10 illustrated in FIGS. 1 and 2 also includes a fastening system 60 to facilitate securing and removing the diaper pant 10 about the waist of the wearer. In the illustrated embodiment, the fastening system 60 includes a pair of first fastener assemblies 62 disposed on the rear panel 38 and a pair of second fastener assemblies 64 disposed on the front panel 36. Each first fastener assembly 62 is configured to matingly engage one of the second fastener assemblies 64 to refastenably secure the diaper pant 10 in the wear configuration (shown in FIG. 2). In other suitable embodiments, the diaper may include only a first pair of fastener assemblies 62 disposed on one of the front panel 36 and rear panel 38, and configured to directly matingly engage the other of the front panel 36 and the rear panel 38. In some embodiments, the diaper pant 10 may be manufactured in a prefastened configuration by attaching the first fastener assemblies 62 to the second fastener assemblies 64 during the manufacturing process.

As seen in FIG. 2, the front region 12 of the diaper pant 10 is joined to the rear region 14 via a pair of refastenable seams 40 to define a pull-on, pant-like configuration of the diaper pant 10 having a waist opening, indicated at 48, and two leg openings, indicated at 50. More specifically, the front panel 36 and the rear panel 38 are releasably attached to one another by the fastening system 60. In other suitable embodiments, the front region 12 of the diaper pant 10 can be joined to the rear region 14 via a pair of nonrefastenable side seams (see, e.g., FIG. 4).

With the diaper pant 10 in the pull-on, pant-like (or wear) configuration, illustrated in FIG. 2, the front region 12 comprises the portion of the diaper pant 10 which, when worn, is positioned at least in part on the front of the wearer while the rear region 14 comprises the portion of the diaper pant 10 which is positioned at least in part on the back of the wearer. The crotch region 16 of the diaper pant 10 comprises the portion of the diaper pant 10 which is positioned between the legs of the wearer and covers the lower torso of the wearer.

As shown in FIGS. 1 and 2, the diaper pant 10 also includes a gripping or seam-separating feature shown in the form of a pair of integrally formed finger tabs 66. The finger tabs 66 facilitate removal of the diaper pant 10 by facilitating manual separation of the seams 40. In particular, the finger tabs 66 provide the wearer with a tab that enables the wearer to easily apply a peeling or tearing force to the seams 40 of the diaper pant 10. As described in more detail herein, the method of manufacturing the diaper pant 10 facilitates integrally forming the finger tabs 66 with one or both of the front panel 36 and the rear panel 38, reducing the number of steps and complexity of the manufacturing process as compared to processes used to manufacture diaper pants having finger or grip tabs formed separately from and attached to the diaper pant.

Still referring to FIGS. 1 and 2, the central absorbent assembly 34 is configured to contain and/or absorb exudates discharged from the wearer. The outer cover 42 suitably comprises a material which is substantially liquid impermeable. The outer cover 42 can be a single layer of liquid impermeable material, but more suitably comprises a multi-layered laminate structure in which at least one of the layers is liquid impermeable.

The inner layer of the outer cover 42 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 42 when a single layer, prevents waste material from wetting articles, such as bed sheets and clothing, as well as the wearer and caregiver.

If the outer cover 42 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 42. One suitable "breathable" material is composed of a microporous polymer film or a nonwoven fabric that has been coated or otherwise treated to impart a desired level of liquid impermeability.

The liquid permeable bodyside liner 44 is illustrated as overlying the outer cover 42 and absorbent structure 46, and may, but need not, have the same dimensions as the outer cover 42. The bodyside liner 44 is suitably compliant, soft feeling, and non-irritating to the wearer's skin. The bodyside liner 44 is also sufficiently liquid permeable to permit liquid body exudates to readily penetrate through its thickness to the absorbent structure 46. Further, the bodyside liner 44 can be less hydrophilic than the absorbent structure 46 to present a relatively dry surface to the wearer and permit liquid to readily penetrate through its thickness. The hydrophilic/hydrophobic properties can be varied across the length, width and/or depth of the bodyside liner 44 and absorbent structure 46 to achieve the desired wetness sensation or leakage performance.

The bodyside liner 44 can be manufactured from a wide selection of web materials, such as porous foams, reticulated foams, apertured plastic films, woven and nonwoven webs, or a combination of any such materials. For example, the bodyside liner 44 may comprise a meltblown web, a spun-bonded web, or a bonded-carded-web composed of natural fibers, synthetic fibers or combinations thereof. The bodyside liner 44 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 44 or can be selectively applied to particular sections of the bodyside liner 44, such as the medial section along the longitudinal center line.

The absorbent structure 46 is suitably compressible, conformable, non-irritating to a wearer's skin, and capable of absorbing and retaining liquids and certain body wastes. For example, the absorbent structure 46 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials may be formed into a web structure by employing various conventional methods and techniques. For example, the absorbent structure 46 may be formed by a dry-forming technique, an air forming technique, a wet-forming technique, a foam-forming technique, or the like, as well as combinations thereof. Furthermore, the absorbent structure 46 may itself encompass multiple layers in a Z-direction (e.g., thickness) of the absorbent structure 46. Such multiple layers may take advantage of differences in absorbent capacity, such as by placing a lower absorbent capacity material layer closer to the bodyside liner 44 and a higher absorbent capacity material closer to the outer cover 42. Likewise, discrete portions of a single-layered absorbent structure may encompass higher capacity absorbents, and other discrete portions of the structure may encompass lower capacity absorbents.

In one suitable embodiment, superabsorbent material is present in the absorbent structure 46 in an amount of from about 0 to about 100 weight percent based on total weight of the absorbent structure 46. The absorbent structure 46 may suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid.

The absorbent structure 46 may comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene.

The absorbent assembly 34 may also include a surge management layer (not shown) located adjacent the absorbent structure 46 (e.g., between the absorbent structure 46 and the bodyside liner 44) to help decelerate and diffuse surges or gushes of liquid that may be rapidly introduced into the absorbent structure 46 of the diaper pant 10 by the wearer. Desirably, the surge management layer can rapidly accept and temporarily hold the liquid prior to releasing the liquid into the storage or retention portions of the absorbent structure 46. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al, all of which are hereby incorporated by reference in their entirety.

The absorbent assembly 34 may also include a pair of containment flaps (not shown) that extend longitudinally along the absorbent assembly 34 and are adapted to provide a barrier to the lateral flow of body exudates as is known in the art. The containment flaps can be connected to the bodyside liner 44 or other components of the absorbent assembly 34. Suitable configurations of the containment flaps are described, for example, in U.S. Pat. No. 5,599,338 issued Feb. 4, 1997, to K. Enloe, which is hereby incorporated by reference in its entirety.

The front panel 36 can be formed from a single piece of material, or can be formed as a laminate consisting of two or more layers. The layers of the laminate can be of the same material or different material. In one embodiment, the front panel 36 comprises a laminate formed from two or more elastic strands disposed between two nonwoven layers. The nonwoven layers may be single layer nonwovens, such as spunbond webs, or nonwoven laminates, such as spunbond laminates (e.g., spunbond/spunbond/spunbond (SSS)) and spunbond/meltblown laminates (e.g., spunbond/meltblown/spunbond (SMS)). The elastic strands can be formed from LYCRA® (commercially available from Invista of Wichita, Kans., U.S.A.), or a similar material. The diameter and/or cross-sectional configuration of the elastic strands, the decitex (weight in grams per 10,000 meters) of the elastic strands, the spacing between elastic strands, and the tension imparted into the elastic strands can all be varied to suit particular product needs. The exact number of elastic strands that are utilized should be sufficient to ensure that the diaper pant 10 snuggly conforms to the wearer's torso.

In other embodiments, the front panel 36 comprises an elastomeric film disposed between two nonwoven facing layers. One example of an elastomeric film laminate is described in U.S. Pat. No. 7,803,244 issued Sep. 28, 2010 to Siqueira et al., which is hereby incorporated by reference in its entirety.

The front panel 36 can be formed from a breathable or a non-breathable material. In some embodiments, the front panel 36 is formed from a breathable material, or a material that is treated or processed to be breathable. Suitable breathable materials include, but are not limited to, spunbond webs, bonded carded webs, and spunbond/meltbown/spunbond laminates. Other suitable materials from which the front panel 36 can be formed include woven and non-woven materials formed from natural or synthetic fibers; polyolefins, such as polypropylene or polyethylene; thermoplastic films; as well as other materials known to those skilled in the art.

In the illustrated embodiment, the front panel 36 is formed by a single continuous sheet or laminate that extends from the first front side edge 20 of the front region 12 to the second front side edge 22 of the front region.

The rear panel 38 may be constructed from the same materials and have the same configuration as the front panel 36. That is, the rear panel 38 can be formed from a single piece of material, or can be formed as a laminate consisting of two or more layers. The rear panel 38 may comprise a laminate formed from two or more elastic strands disposed between two nonwoven layers. In other embodiments, the rear panel 38 may comprise an elastomeric film disposed between two nonwoven facing layers.

The rear panel 38 can be formed from a breathable or a non-breathable material. In some embodiments, the rear panel 38 is formed from a breathable material, or a material that is treated or processed to be breathable. Other suitable materials from which the rear panel 38 can be formed include woven and non-woven materials formed from natural or synthetic fibers; polyolefins, such as polypropylene or polyethylene; thermoplastic films; as well as other materials known to those skilled in the art.

In the illustrated embodiment, the rear panel 38 is formed by a single continuous sheet or laminate that extends from the first rear side edge 26 of the rear region 14 to the second rear side edge 28 of the rear region 14.

The first fastener assemblies 62 comprise first fastening components 68 configured to repeatedly engage and disengage a second fastening component 70 of the second fastener assemblies 64. In one embodiment, one surface of each of the fastening components 68, 70 includes a plurality of engaging elements disposed on that surface. For example, in one suitable embodiment, the first fastening components 68 each include female fasteners, such as loop type fasteners, and the second fastening components 70 each include complementary male fasteners, such as hook type fasteners. In another suitable embodiment, such as the embodiment shown in FIGS. 1 and 2, the first fastening components 68 each include male fasteners and the second fastening components 70 each include complementary female fasteners.

Loop type fasteners typically include a fabric or material having a base or backing structure and a plurality of loop members extending outwardly from at least one surface of the backing structure. The loop material can be formed of any suitable material, such as acrylic, nylon or polyester, and can be formed by methods such as warp knitting, stitch bonding or needle punching. One particular suitable loop type fastener is a pattern-unbonded (PUB) nonwoven web. Examples of suitable PUB materials are described in U.S. Pat. No. 5,858,515 issued to Stokes et al. on Jan. 12, 1999, and U.S. Pat. No. 6,921,570 issued to Belau et al. on Jul. 26, 2005, the disclosures of which are hereby incorporated by reference in their entirety.

Hook type fasteners typically include a fabric or material having a base or backing structure and a plurality of hook members extending outwardly from at least one surface of the backing structure. The hook material may include a resilient material to minimize unintentional disengagement of the fastener components as a result of the hook material becoming deformed. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable hook materials are available from Velcro USA Inc., Manchester, N.H., U.S.A., or affiliates thereof.

In the illustrated embodiment, each of the first fastening components 68 comprises a strip of hook-type material configured for releasable attachment with the second fastening components 70. Further, each of the fastening components 68 are disposed on respective carrier sheets 72 that are attached to the rear panel 38. More specifically, each carrier sheet 72 is attached to the body-facing side of the rear panel 38 along one of the first or second rear side edges 26, 28 by any suitable means such as, for example, adhesives, ultrasonic bonds, thermal bonds, pressure bonds, or combinations thereof. More particularly, each carrier sheet 72 includes a first, fixed edge 74 attached to the rear panel 38, and a second, free edge 76 opposite the first edge 74. In the illustrated embodiment, the first edge 74 of each carrier sheet 72 is coterminous with one of the rear side edges 26, 28 of the rear region 14, although in other embodiments the first edge 74 may be spaced from a corresponding side edge 26 or 28 of the rear region. Each first fastening component 68 is attached to one of the carrier sheets 72 by suitable means such as, for example, adhesives, ultrasonic bonds, thermal bonds, pressure bonds, or combinations thereof. Further, each first fastening component 68 is attached proximate the free edge 76 of the respective carrier sheet 72 such that the first fastening components 68 can be moved away from the body-facing side of the rear panel 38 when the diaper pant 10 is in the wear configuration (shown in FIG. 2). As a result, forces imparted on the fastening system 60 during wear of the diaper pant 10 tend to have a greater shearing component (i.e., parallel to the plane of the fastening components 68, 70) rather than a tensile or peel component (i.e., perpendicular to the plane of the fastening components 68, 70), thereby reducing the likelihood of the seams 40 unintentionally opening.

In other embodiments, the first fastening components 68 may be attached directly to the body-facing side of the rear panel 38 (i.e., without an interconnecting carrier sheet). In such embodiments, one or both of the first fastening components 68 may comprise a sheet of fastening material (e.g., hook type or loop type material) having a first, or fixed edge coterminous with one of the rear side edges 26, 28 of the rear region 14, and a second, or free edge opposite the fixed edge. Additionally or alternatively, one or both of the second fastening components 70 may comprise a sheet of complementary fastening material (e.g., loop type or hook type material) having a first, or fixed edge coterminous with one of the front side edges 20, 22 of the front region 12, and a second, or free edge opposite the fixed edge. Suitably, in embodiments where one of the first fastening components 68 and the second fastening components 70 have a free edge, the other of the first fastening components 68 and the second fastening components 70 have both edges fixed to a corresponding front panel 36 or rear panel 38.

In the illustrated embodiment, each of the second fastening components 70 comprises a sheet of loop-type fastening material attached to a body-facing surface of the front panel 36. The second fastening components 70 are attached to the front panel 36 by suitable means such as adhesives, ultrasonic bonds, thermal bonds, pressure bonds, or combinations thereof. One of the second fastening components 70 extends to and is coterminous with the first front side edge 20, and the other second fastening component 70 extends to and is coterminous with the second front side edge 22. In the illustrated embodiment, each of the second fastening components 70 is attached to the front panel 36 over the entire surface of the second fastening component 70. In other embodiments, the second fastening components 70 may comprise a strip of fastening material (e.g., loop type or hook type material) spaced from respective side edges 20, 22 of the front region 12.

As noted above, the diaper pant 10 includes integrally formed finger tabs 66 that facilitate manually separating the refastenable seams 40 to remove the diaper pant 10 from the wearer. The term "integrally formed" as used herein with reference to finger tabs means that the finger tabs are formed unitarily or continuously with the panel from which the finger tabs extend, rather than being formed separately and being bonded to, placed with, or placed near the panel. In the embodiment illustrated in FIG. 1, for example, the finger tabs 66 are formed from the same web or sheet of material from which the front panel 36 is formed.

The finger tabs 66 extend transversely outward from the front panel 36 along the first and second side edges 20, 22, and are suitably sized and shaped to permit a user to grasp the finger tabs 66 and apply a peeling or tearing force thereto. In the illustrated embodiment, each finger tab 66 has a generally arcuate shape, and more specifically, a semi-circular shape, although it is contemplated that the finger tabs 66 may have any suitable shape that enables the finger tabs 66 to function as described herein. In one suitable embodiment, for example, the finger tabs 66 have a generally square, triangular, or rectangular shape.

Each finger tab 66 is partially defined by a cutout 78 that extends transversely inward into the front panel 36 along one of the first and second front side edges 20, 22. Each cutout 78 is shaped complementary to the corresponding finger tab 66 partially defined by the cutout 78. Further, each cutout 78 is shaped complementary to the finger tab 66 disposed on the opposite side edge of the front panel 36 from the cutout 78.

As shown in FIGS. 1 and 2, the finger tab 66 disposed on the first front side edge 20 is longitudinally offset (i.e., in the longitudinal direction 30 of the diaper pant 10) from the finger tab 66 disposed on the second front side edge 22. Further, the finger tab 66 disposed on the first front side edge 20 is laterally aligned (i.e., in the lateral direction 32 of the diaper pant 10) with the cutout 78 disposed on the second front side edge 22, and the finger tab 66 disposed on the second front side edge 22 is laterally aligned with the cutout 78 disposed on the first front side edge 20. As shown in FIGS. 1 and 2, the finger tabs 66 and the cutouts 78 give the first and second front side edges 20, 22 an oscillating or undulating appearance.

In other suitable embodiments, the finger tab 66 on one side of the front panel 36 may be other than laterally aligned with the cutout 78 on the opposite side edge of the front panel 36, and/or the finger tab 66 on one side edge of the front panel 36 may be other than longitudinally offset from the finger tab 66 on the other side edge of the front panel 36.

In use, the prefastened diaper pant 10 is donned by inserting a user's legs through the leg openings 50, and sliding the diaper pant 10 up and around the user's waist. To remove the diaper pant 10 from a wearer (e.g., after the diaper pant 10 is soiled with body exudates), the refastenable seams 40 are separated by grasping and pulling the finger tabs 66 away from the carrier sheet 72 with a sufficient force to overcome the engagement between the first fastener assemblies 62 and the second fastener assemblies 64. The diaper pant 10 can then be removed from the wearer.

Although the illustrated diaper pant 10 is illustrated as including finger tabs 66 on the front panel 36, it is contemplated that the diaper pant 10 may include finger tabs 66 on the rear panel 38, in addition to or as an alternative to the finger tabs 66 on the front panel 36.

Figure 3:
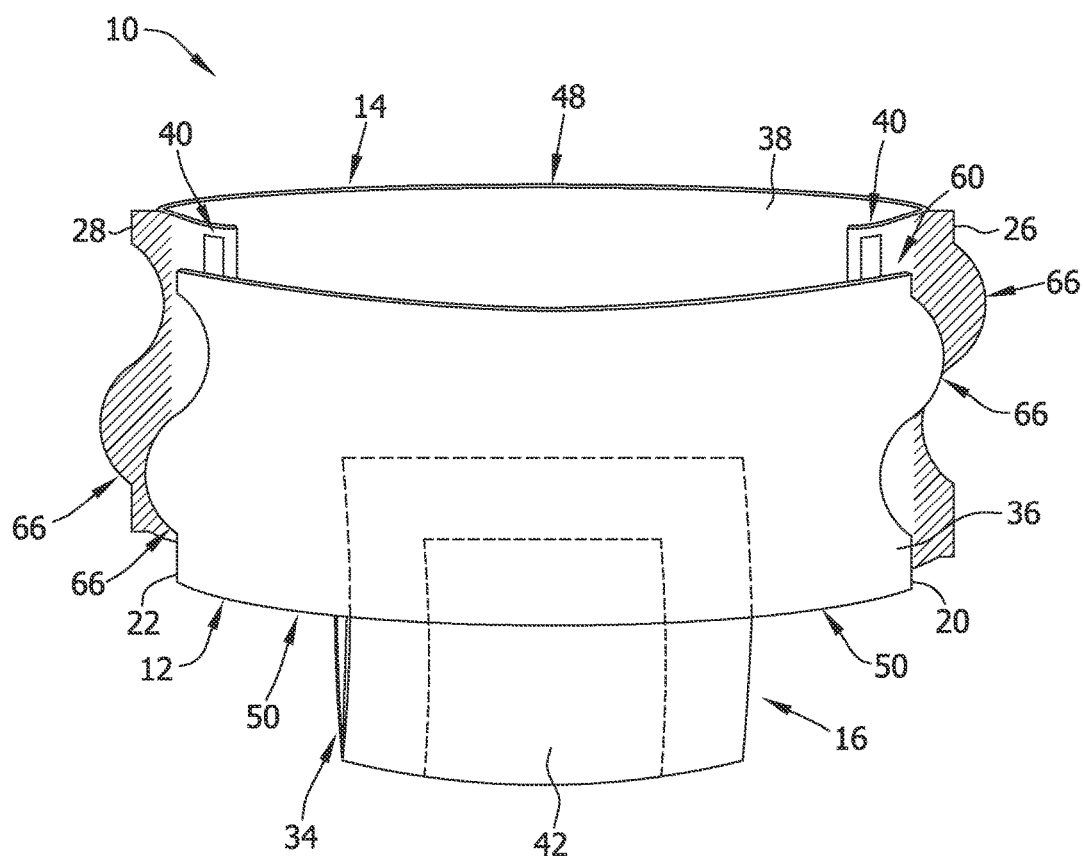
FIG. 3 is a front view of the diaper pant of FIG. 2 having finger tabs on a front panel and a rear panel of the diaper pant.

In the embodiment illustrated in FIG. 3, for example, the diaper pant 10 includes finger tabs 66 on each of the first and second rear side edges 26, 28, in addition to the finger tabs 66 on the first and second front side edges 20, 22. In this embodiment, the refastenable seams 40 can be separated by grasping one of the finger tabs 66 on the front panel 36 with one hand, grasping one of the finger tabs 66 on the rear panel 38 with another hand, and pulling the finger tabs 66 away from one another with sufficient force to separate the refastenable seam 40. Alternatively, the refastenable seams 40 may be separated by pulling one of the finger tabs 66 on the front panel 36 or the rear panel 38 away from the seam 40.

Figure 4:
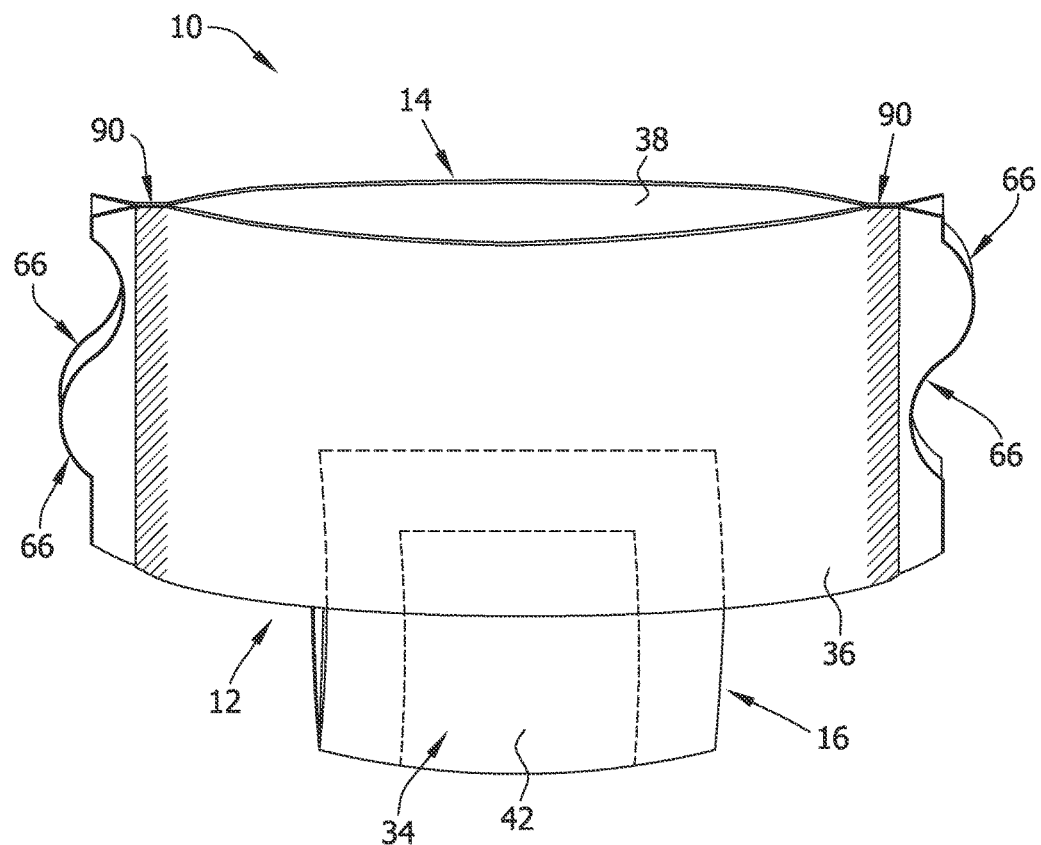
FIG. 4 is a front view of the diaper pant of FIG. 3 having nonrefastenable side seams.

FIG. 4 is a front view of the diaper pant 10 with nonrefastenable side seams 90. More specifically, the front panel 36 is permanently joined to the rear panel 38 along seams 90 by suitable means such as adhesives, ultrasonic bonds, thermal bonds, pressure bonds, and combinations thereof. The term "permanently joined" is synonymous with terms such as "permanently attached," "permanently adhered," and "permanently bonded," and is intended herein to refer to an attachment that is generally not releasable without some damage or substantially reduced functionality of the components that are permanently attached to the absorbent article.

Figure 5:
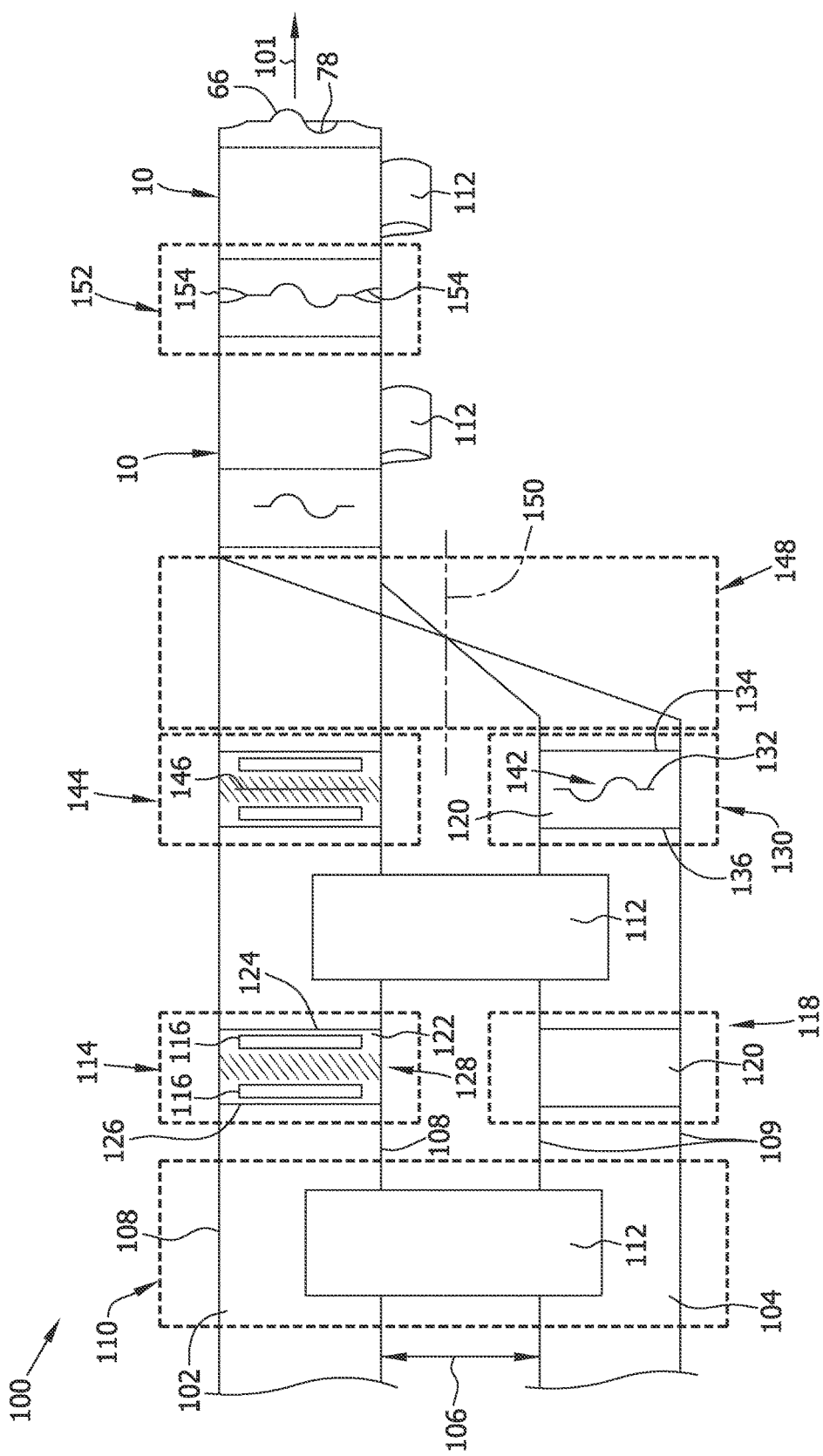
FIG. 5 is a schematic illustrating one suitable method of manufacturing the diaper pant of FIGS. 1 and 2.

FIG. 5 schematically illustrates one suitable method 100 of manufacturing the diaper pant 10 shown in FIGS. 1 and 2.

The method 100 includes feeding a first web 102 of material in a machine direction 101, and feeding a second web 104 of material in the machine direction 101. The first web 102 and the second web 104 are fed from respective supply sources (not shown). Any suitable apparatus may be used to feed the first web 102 and the second web 104 in the machine direction 101, including, but not limited to, nip rolls, tensioning rolls, and combinations thereof.

As shown in FIG. 5, the first web 102 and second web 104 are spaced from one another while they are fed in the machine direction 101. That is, the first web 102 is spaced from the second web 104 by a gap 106 in the cross-machine direction (i.e., the direction substantially perpendicular to the machine direction 101). The gap 106 between first web 102 and second web 104 may have substantially the same dimensions as the gap 52 between the front panel 36 are the rear panel 38 (all shown in FIG. 1). Each of the first web 102 and the second web 104 includes laterally opposing side edges 108 and 109, respectively, extending in the machine direction 101.

The first web 102 of material may be constructed from the same materials as the front panel 36 and the rear panel 38 described above. That is, the first web 102 of material can be formed from a single piece of material, or can be formed as a laminate consisting of two or more layers. The layers of the laminate can be of the same material or different material. In one embodiment, the first web 102 comprises an elastomeric laminate formed from two or more elastic strands disposed between two nonwoven facing layers. The nonwoven layers may be single layer nonwovens, such as spunbond webs, or nonwoven laminates, such as spunbond laminates (e.g., spunbond/spunbond/spunbond (SSS)) and spunbond/meltblown laminates (e.g., spunbond/meltblown/spunbond (SMS)). The elastic strands can be formed from LYCRA® (commercially available from Invista of Wichita, Kans., U.S.A.), or a similar material. The diameter and/or cross-sectional configuration of the elastic strands, the decitex (weight in grams per 10,000 meters) of the elastic strands, the spacing between elastic strands, and the tension imparted into the elastic strands can all be varied to suit particular product needs. The exact number of elastic strands that are utilized should be sufficient to ensure that the diaper pant 10 snuggly conforms to the wearer's torso.

In other embodiments, the first web 102 comprises an elastomeric film disposed between two nonwoven facing layers. One example of an elastomeric film laminate is described in U.S. Pat. No. 7,803,244 issued Sep. 28, 2010 to Siqueira et al.

The first web 102 of material can be formed from a breathable or a non-breathable material. In some embodiments, the first web 102 is formed from a breathable material, or a material that is treated or processed to be breathable. Suitable breathable materials include, but are not limited to, spunbond webs, bonded carded webs, and SMS laminates. Other suitable materials from which the first web 102 can be formed include woven and non-woven materials formed from natural or synthetic fibers; polyolefins, such as polypropylene or polyethylene; thermoplastic films; as well as other materials known to those skilled in the art.

The second web 104 of material may comprise the same materials as the first web 102. In some embodiments, the second web 104 of material is the same material as the first web 102 of material. In other embodiments, the second web 104 of material is a different material that than the first web 102 of material.

In the illustrated embodiment, the first web 102 of material defines the rear panel 38 of the diaper pant 10 (shown in FIG. 1) and the second web 104 of material defines the front panel 36 (shown in FIG. 1). In other embodiments, the first web 102 may define the front panel 36 (shown in FIG. 1) and the second web may define the rear panel 38 (shown in FIG. 1).

The method 100 further includes attaching an absorbent assembly 112 to the first web 102 and the second web 104 at an absorbent assembly attachment station 110. The absorbent assembly 112 may have the same construction and comprise the same materials as the absorbent assembly 34 described above with reference to FIGS. 1 and 2. In some embodiments, the absorbent assembly 112 is adhesively bonded to the first web 102 and the second web 104. In such embodiments, adhesive is applied to the first web 102, the second web 104, and/or the absorbent assembly 112 prior to the absorbent assembly 112 being attached to the first web 102 and the second web 104. In other embodiments, attaching the absorbent assembly 112 to the first web 102 and the second web 104 at the absorbent assembly attachment station 110 includes ultrasonic bonding, thermal bonding, pressure bonding, and combinations thereof. The absorbent assembly attachment station 110 may include any suitable apparatus to attach the absorbent assembly 112 to the first web 102 and the second web 104, including, but not limited to, adhesive applicators, compression rolls, nip rolls, laminator rolls, chill rolls, ultrasonic horns, anvils, and combinations thereof.

As shown in FIG. 5, the absorbent assembly 112 spans or bridges the gap 106 separating the first web 102 and the second web 104. The absorbent assembly 112 is attached to the first web 102 and the second web 104 while the webs are moving in the machine direction 101.

As shown in FIG. 5, the method 100 further includes attaching a first fastening component 116 to the first web 102 at a first fastening component attachment station 114, and attaching a second fastening component 120 to the second web 104 at a second fastening component attachment station 118. The first and second fastening components 116, 120 are configured to be releasably attached to one another, and may comprise the same materials and configurations as the first and second fastening components 68, 70 described above. The first fastening component 116 is attached to the first web 102 using suitable means such as adhesives, ultrasonic bonds, thermal bonds, pressure bonds, or combinations thereof. The second fastening component 120 is attached to the second web 104 using suitable means such as adhesives, ultrasonic bonds, thermal bonds, pressure bonds, or combinations thereof. The fastening component attachment stations 114, 118 may include any suitable apparatus to attach the first fastening component 116 to the first web 102 and the second fastening component 120 to the second web 104, including, but not limited to, adhesive applicators, compression rolls, nip rolls, laminator rolls, chill rolls, ultrasonic horns, anvils, and combinations thereof. In the illustrated embodiment, two first fastening components 116 are attached to the first web 102 at the first fastening component attachment station 114. The first fastening components 116 may be attached in a single step (i.e., simultaneously), or in separate steps (i.e., individually).

In some embodiments, such as the embodiment illustrated in FIG. 5, attaching the first fastening component 116 to the first web 102 includes attaching a carrier sheet 122 to the first web 102, and attaching the first fastening component 116 to the carrier sheet 122. As shown in FIG. 5, the carrier sheet 122 includes a leading edge 124 and a trailing edge 126, and is bonded to the first web 102 such that the leading edge 124 and the trailing edge 126 are free edges. In the illustrated embodiment, the carrier sheet 122 is bonded to the first web 102 along a bond zone 128 located approximately midway between the leading edge 124 and the trailing edge 126 of the carrier sheet 122, leaving the leading edge 124 and trailing edge 126 as free edges. As shown in FIG. 5, a pair of first fastening components 116 is attached to the carrier sheet 122. In the illustrated embodiment, one of the first fastening components 116 is attached proximate the leading free edge 124 of the carrier sheet 122, and the other first fastening component 116 is attached proximate the trailing free edge 126 of the carrier sheet 122. In other suitable embodiments, the first fastening components 116 may be attached to the carrier sheet 122 at any suitable location between the bond zone 128 and one of the leading edge 124 and the trailing edge 126. The first fastening components 116 may be attached to the carrier sheet 122 after the carrier sheet 122 is attached to the first web 102 or, as shown in FIG. 5, the first fastening components 116 may be attached to the carrier sheet 122 before the carrier sheet 122 is attached to the first web 102.

The method 100 further includes forming a partial cut line 132 through the second web 104 at a first cutting station 130. The term "partial cut line" refers to a cut line that does not completely sever the second web 104 into two separate pieces. The partial cut line 132 may extend through the entire thickness of the second web 104, but does not extend continuously from one side edge 109 to the other side edge 109. In the illustrated embodiment, the partial cut line 132 is spaced from each of the side edges 109 of the second web 104. The first cutting station 130 may include any suitable apparatus to form the partial cut line 132 in the second web 104, including, but not limited to, knife rolls and anvil rolls.

The partial cut line 132 is formed through both the second web 104 and the second fastening component 120. The partial cut line 132 is located approximately midway between a leading edge 134 of the second fastening component 120 and a trailing edge 136 of the second fastening component 120.

As shown in FIG. 5, the partial cut line 132 defines a finger tab 66 and a cutout 78 on the diaper pant 10 when the diaper pant 10 is formed. More specifically, the partial cut line 132 defines a finger tab 66 and a cutout 78 on two separate diaper pants 10—i.e., a leading diaper pant and a trailing diaper pant. To form a finger tab 66 on both a leading diaper pant and the trailing diaper pant, the partial cut line 132 includes an undulated region 142. The undulated region 142 defines a finger tab 66 and a cutout 78 on both the leading diaper pant 10 and the trialing diaper pant 10. In the illustrated embodiment, the partial cut line 132 has rounded undulations, giving the undulated region 142 the appearance of a sinusoidal wave, although it is understood that the partial cut line 132 may have any suitable configuration that forms a finger tab 66 on a leading diaper pant 10 and a trailing diaper pant 10. In other suitable embodiments, for example, the partial cut line 132 may have square-shaped undulations, giving the undulated region 142 the appearance of a square wave, or triangular-shaped undulations, giving the undulated region 142 the appearance of a zigged-zagged line. In yet other suitable embodiments, the partial cut line 132 may define a finger tab 66 and/or a cutout 78 on only one diaper pant. In one suitable embodiment, for example, a first partial cut line 132 defines a finger tab 66 and a cutout 78 on the trailing edge of a leading diaper pant 10, and a second partial cut line 132 defines a finger tab 66 and a cutout 78 on the leading edge of a tailing diaper pant 10.

In the illustrated embodiment, the partial cut line 132 is formed through the second web 104 after the absorbent assembly 112 is attached to the first and second webs 102, 104. In other suitable embodiments, the partial cut line 132 may be formed prior to attaching the absorbent assembly 112 to the first and second webs 102, 104.

As shown in FIG. 5, the method 100 also includes forming a cut line 146 through the first web 102 at a second cutting station 144. As shown in FIG. 5, the cut line 146 is a partial cut line. The second cutting station 144 may include any suitable apparatus to form the cut line 146 in the first web 102, including, but not limited to, knife rolls and anvil rolls.

In the illustrated embodiment, the cut line 146 in the first web 102 is formed generally midway between a pair of first fastening components 116, and is formed through both the first web 102 and the carrier sheet 122. More specifically, the cut line 146 is formed along a bond zone 128 used to attach the carrier sheet 122 to the first web 102. The illustrated cut line 146 is a substantially straight line extending generally perpendicular to the machine direction 101, although it is contemplated that the cut line 146 may have other shapes and orientations.

As shown in FIG. 5, the method 100 further includes folding the first web 102 into face-to-face relationship with the second web 104 at a folding station 148 after forming the partial cut line 132 and the cut line 146. Folding the first web 102 into face-to-face relationship with the second web 104 at the folding station 148 causes the first fastening components 116 to be releasably fastened to the second fastening components 120, thereby providing a pre-fastened diaper pant 10. When the first web 102 is folded into face-to-face relationship with the second web 104, the partial cut line 132 in the second web 104 is substantially aligned with the cut line 146 in the first web 102.

Folding the first web 102 into face-to-face relationship with the second web 104 includes rotating one of the first web 102 and the second web 104 about a fold line 150 extending parallel to the machine direction 101. In the illustrated embodiment, the second web 104 is shown as being rotated about the fold line 150, although it is contemplated that the first web 102 may be rotated about the fold line 150 instead of the second web 104. The folding station 148 may include any suitable folding mechanism to fold the first web 102 in to face-to-face relationship with the second web 104.

The method 100 further includes cutting the first web 102 and the second web 104 at a third cutting station 152 while the first and second webs 102, 104 are in face-to-face relationship to separate a leading diaper pant 10 from a trailing diaper pant 10. As shown in FIG. 5, the partial cut line 132 formed in the second web 104 defines a finger tab 66 on each of the leading diaper pant 10 and the trailing diaper pant 10. The partial cut line 132 also defines a cutout 78 in each of the diaper pants 10. The third cutting station 152 may include any suitable apparatus to cut the first web 102 and the second web 104, including, but not limited to, knife rolls and anvil rolls.

In the illustrated embodiment, cutting the first and second webs 102, 104 at the third cutting station 152 includes forming cutouts 154 along the laterally opposing side edges 108 and 109 of each of the first web 102 and the second web 104. The cutouts 154 intersect the partial cut line 132 formed in the second web 104, and the cut line 146 formed in the first web 102, thereby forming a continuous cut line that extends across each of the first web 102 and the second web 104. In other suitable embodiments, cutting the first and second webs 102, 104 may include forming a cutout 154 along only one of the side edges 108 or 109 of the first and second webs 102, 104. In yet other suitable embodiments, cutting the first and second webs 102, 104 may include forming one or more linear cut lines that intersect the partial cut line 132 and the cut line 146 to form continuous cut lines that extend across each of the first web 102 and the second web 104.

The method 100 illustrated in FIG. 5 provides integrally formed finger tabs 66 that facilitate separating the refastenable seams 40 of the diaper pant 10 (shown in FIGS. 1 and 2) when a user desires to remove the diaper pant 10. Forming a partial cut line 132 in the second web 104, as opposed to a full cut line, enables the finger tabs 66 to be selectively formed on only one of the front panel 36 and the rear panel 38 of the diaper pant 10, depending on which panel is formed from the second web 104. In the illustrated embodiment, the second web 104 forms the front panel 36 of the diaper pant 10, and thus the finger tabs 66 are formed on the front panel 36. In other embodiments, the finger tabs 66 may be formed on the rear panel 38, for example, by forming the rear panel 38 of the diaper pant 10 from the second web 104. In another suitable embodiment, the partial cut line 132 may be formed in the first web 102, and the cut line 146 may be formed in the second web 104.

Figure 6:
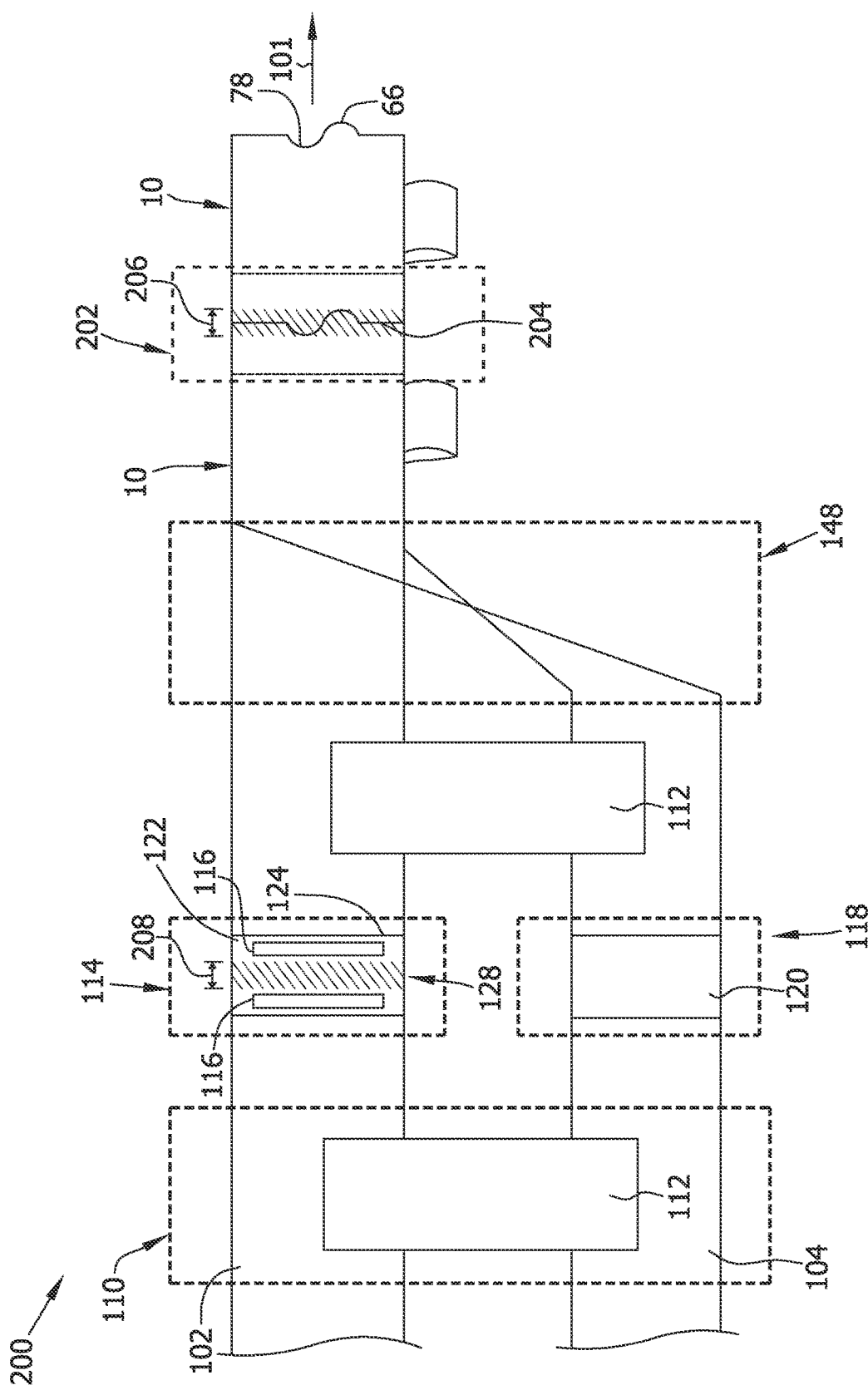
FIG. 6 is a schematic illustrating one suitable method of manufacturing the diaper pant of FIG. 3.

FIG. 6 schematically illustrates one suitable method 200 of manufacturing the diaper pant 10 shown in FIG. 3 having finger tabs 66 on the front panel 36 and the rear panel 38. The method 200 illustrated in FIG. 6 is substantially identical to the method 100 shown in FIG. 5, except the method 200 of FIG. 6 utilizes a one-step cutting process to form finger tabs 66 on both the front panel 36 and the rear panel 38 of the diaper pant 10 (shown in FIG. 3).

More specifically, the method 200 includes feeding the first web 102 of material in the machine direction 101, feeding the second web 104 of material in the machine direction 101, attaching the absorbent assembly 112 to the first web 102 and the second web 104 at the absorbent assembly attachment station 110, folding the first web 102 into face-to-face relationship with the second web 104 at the folding station 148, and cutting the first and second webs 102, 104 at a cutting station 202 while the first and second webs 102, 104 are in face-to-face relationship.

The first web 102 and the second web 104 may have substantially the same construction as described above with reference to FIG. 5. Further, feeding the first web 102 in the machine direction 101, feeding the second web 104 in the machine direction, attaching the absorbent assembly 112 to the first web 102 and the second web 104 at the absorbent assembly attachment station 110, and folding the first web 102 into face-to-face relationship with the second web 104 at the folding station 148 may be carried out in the same manner as described above with reference to FIG. 5.

As shown in FIG. 6, the method 200 may also include attaching a first fastening component 116 to the first web 102 at the first fastening component attachment station 114, and attaching a second fastening component 120 to the second web 104 at the second fastening component attachment station 118, both of which may be carried out in the same manner as described above with reference to FIG. 5.

Cutting the first web 102 and the second web 104 at the cutting station 202 includes forming an undulated cut line 204 that extends through both the first web 102 and the second web 104. In the illustrated embodiment, the undulated cut line 204 also extends through the carrier sheet 122 and the second fastening component 120.

As shown in FIG. 6, cutting the first and second webs 102, 104 with the undulated cut line 204 separates a leading diaper pant 10 from a trailing diaper pant 10, and forms a finger tab 66 on each of the leading diaper pant 10 and the trailing diaper pant 10. More specifically, cutting the first and second webs 102, 104 at the cutting station 202 forms a finger tab 66 on both the front panel 36 and the rear panel 38 (shown in FIG. 3) of each of the leading diaper pant 10 and the trailing diaper pant 10.

In the illustrated embodiment, the undulated cut line 204 has rounded undulations, giving the cut line 204 the appearance of a sinusoidal wave, although it is understood that cut line 204 may have any suitable configuration that forms a finger tab 66 on a leading diaper pant 10 and a trailing diaper pant 10. In other suitable embodiments, for example, the undulated cut line 204 may have square-shaped undulations, giving the cut line 204 the appearance of a square wave, or triangular-shaped undulations, giving the cut line 204 the appearance of a zigged-zagged line. In yet other suitable embodiments, the undulated cut line 202 may define a finger tab 66 and/or a cutout 78 on only one diaper pant.

As shown in FIG. 6, the undulated cut line 204 has a width 206 in the machine direction 101 defined by the opposite extremes of the cut line 204. The bond zone 128 used to attach the carrier sheet 122 to the first web 102 also has a width 208 in the machine direction 101. The width 206 of the undulated cut line 204 is less than the width 208 of the bond zone 128 to ensure the carrier sheet 122 does not separate from the first web 102 along the first and second rear side edges 26, 28 of the diaper pant 10 (all shown in FIG. 3).

The method 200 illustrated in FIG. 6 provides integrally formed finger tabs 66 on both the front panel 36 and the rear panel 38 of the diaper pant 10 (shown in FIG. 3). The finger tabs 66 facilitate separating the refastenable seams 40 of the diaper pant 10 when a user desires to remove the diaper pant 10. By cutting the first web 102 and the second web 104 with an undulated cut line 204 after the first web 102 is folded into face-to-face relationship with the second web 104, the integral finger tabs 66 can be formed on both the front panel 36 and the rear panel 38 in a one-step cutting process.

Figure 7:
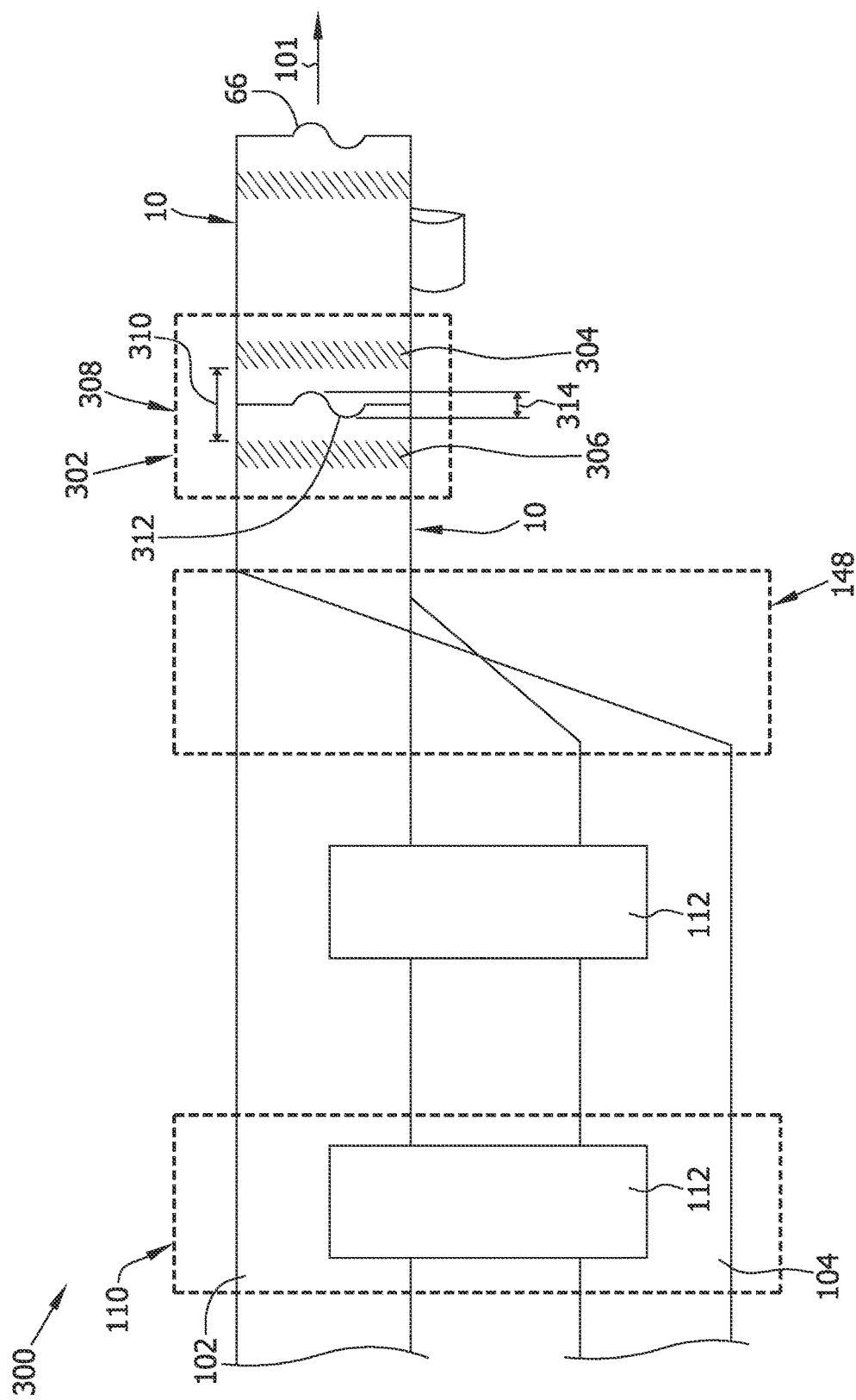
FIG. 7 is a schematic illustrating one suitable method of manufacturing the diaper pant of FIG. 4.

FIG. 7 schematically illustrates one suitable method 300 of manufacturing the diaper pant 10 shown in FIG. 4 having nonrefastenable side seams 90. The method 300 is substantially similar to the method 200 shown in FIG. 6, except the method of FIG. 7 utilizes nonrefastenable side seams to attach the first web 102 to the second web 104. More specifically, the method 300 includes feeding the first web 102 of material in the machine direction 101, feeding the second web 104 of material in the machine direction 101, attaching the absorbent assembly 112 to the first web 102 and the second web 104 at the absorbent assembly attachment station 110, folding the first web 102 into face-to-face relationship with the second web 104 at the folding station 148, bonding the first web 102 to the second web 104 at a first seam 304 and a second seam 306 at a bonding station 302, and cutting the first web 102 and the second web 104 between the first seam 304 and the second seam 306 at a cutting station 308 while the first web 102 and the second web 104 are in face-to-face relationship.

The first web 102 and the second web 104 may have substantially the same construction as described above with reference to FIG. 5. Further, feeding the first web 102 in the machine direction 101, feeding the second web 104 in the machine direction, attaching the absorbent assembly 112 to the first web 102 and the second web 104 at the absorbent assembly attachment station 110, and folding the first web 102 into face-to-face relationship with the second web 104 at the folding station 148 may be carried out in the same manner as described above with reference to FIG. 5.

As shown in FIG. 7, bonding the first web 102 to the second web 104 at the bonding station 302 includes bonding the first web 102 to the second web 104 at the first seam 304 and the second seam 306. The first seam 304 is spaced from the second seam 306 in the machine direction 101 by a distance 310. In particular, the inner edges of the first seam 304 and the second seam 306 are spaced by the distance 310 in the machine direction 101. The first web 102 may be bonded to the second web 104 by any suitable means including adhesives, ultrasonic bonds, thermal bonds, pressure bonds, and combinations thereof. The bonding station 302 may include any suitable apparatus to bond the first web 102 to the second web 104, including, but not limited to, adhesive applicators, compression rolls, nip rolls, laminator rolls, chill rolls, ultrasonic horns, anvils, and combinations thereof.

Cutting the first web 102 and the second web 104 at the cutting station 308 includes cutting the first web 102 and the second web 104 between the first seam 304 and the second seam 306. Cutting the first web 102 and the second web 104 at the cutting station 308 also includes forming an undulated cut line 312 that extends through both the first web 102 and the second web 104.

In the illustrated embodiment, the bonding station 302 and the cutting station 308 are illustrated as a single station. In other words, the steps of bonding the first web 102 to the second web 102 and cutting the first web 102 and the second web 104 are performed at a single station in the illustrated embodiment. In other suitable embodiments, the bonding station 302 and the cutting station 308 may be separate, discrete stations, and the steps of bonding the first web 102 to the second web 104 and cutting the first web 102 and the second web 104 may be performed at different stations. In one suitable embodiment, for example, the first web 102 is bonded to the second web 104 at a bonding station, and subsequently, the first web 102 and the second web 104 are cut at a cutting station.

As shown in FIG. 7, cutting the first and second webs 102, 104 with the undulated cut line 312 separates a leading diaper pant 10 from a trailing diaper pant 10, and forms a finger tab 66 on each of the leading diaper pant 10 and the trailing diaper pant 10. More specifically, cutting the first and second webs 102, 104 forms a finger tab 66 on both the front panel 36 and the rear panel 38 (shown in FIG. 4) of each of the leading diaper pant 10 and the trailing diaper pant 10.

In the illustrated embodiment, the undulated cut line 312 has rounded undulations, giving the cut line 312 the appearance of a sinusoidal wave, although it is understood that cut line 312 may have any suitable configuration that forms a finger tab 66 on a leading diaper pant 10 and a trailing diaper pant 10. In other suitable embodiments, for example, the undulated cut line 312 may have square-shaped undulations, giving the cut line 312 the appearance of a square wave, or triangular-shaped undulations, giving the cut line 312 the appearance of a zigged-zagged line. In yet other suitable embodiments, the undulated cut line 312 may define a finger tab 66 and/or a cutout 78 on only one diaper pant.

As shown in FIG. 7, the undulated cut line 312 has a width 314 in the machine direction 101 defined by the opposite extremes of the cut line 312. The width 314 of the undulated cut line 312 is less than the distance 310 between the first seam 304 and the second seam 306 to ensure the cut line 312 does not sever the side seams 90 of the diaper pant 10 (shown in FIG. 4).

The method 300 illustrated in FIG. 7 provides integrally formed finger tabs 66 on both the front panel 36 and the rear panel 38 of the diaper pant 10 with nonrefastenable side seams 90 (shown in FIG. 4). The finger tabs 66 facilitate separating the nonrefastenable seams 90 of the diaper pant 10 when a user desires to remove the diaper pant 10.

Figure 8:
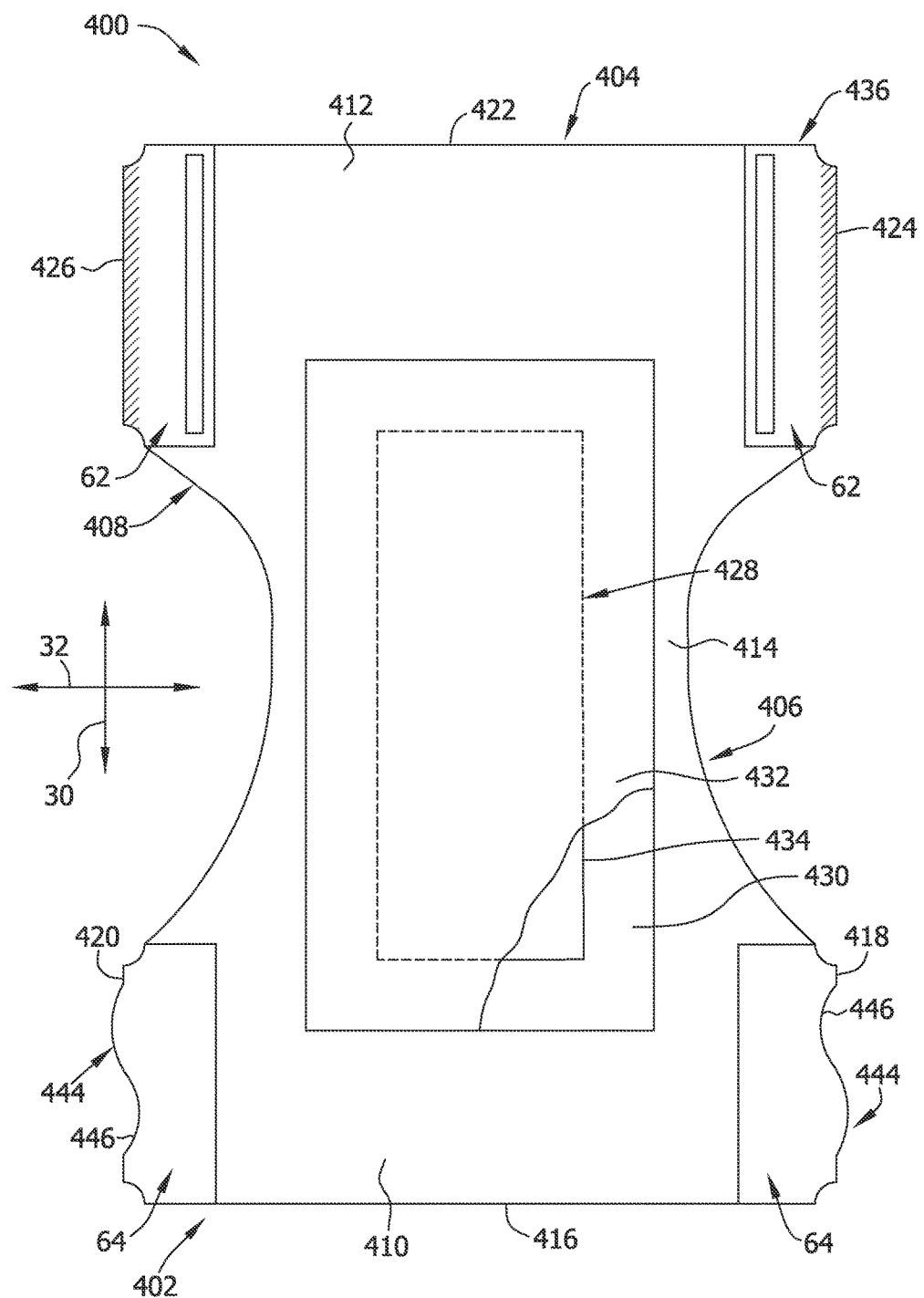
FIG. 8 is a top plan view of another suitable embodiment of an absorbent article according to the present disclosure in the form of a diaper pant, the diaper pant being illustrated in an open and laid flat condition to show an inner surface of the diaper pant that faces towards the wearer when the diaper pant is worn.
Figure 9:
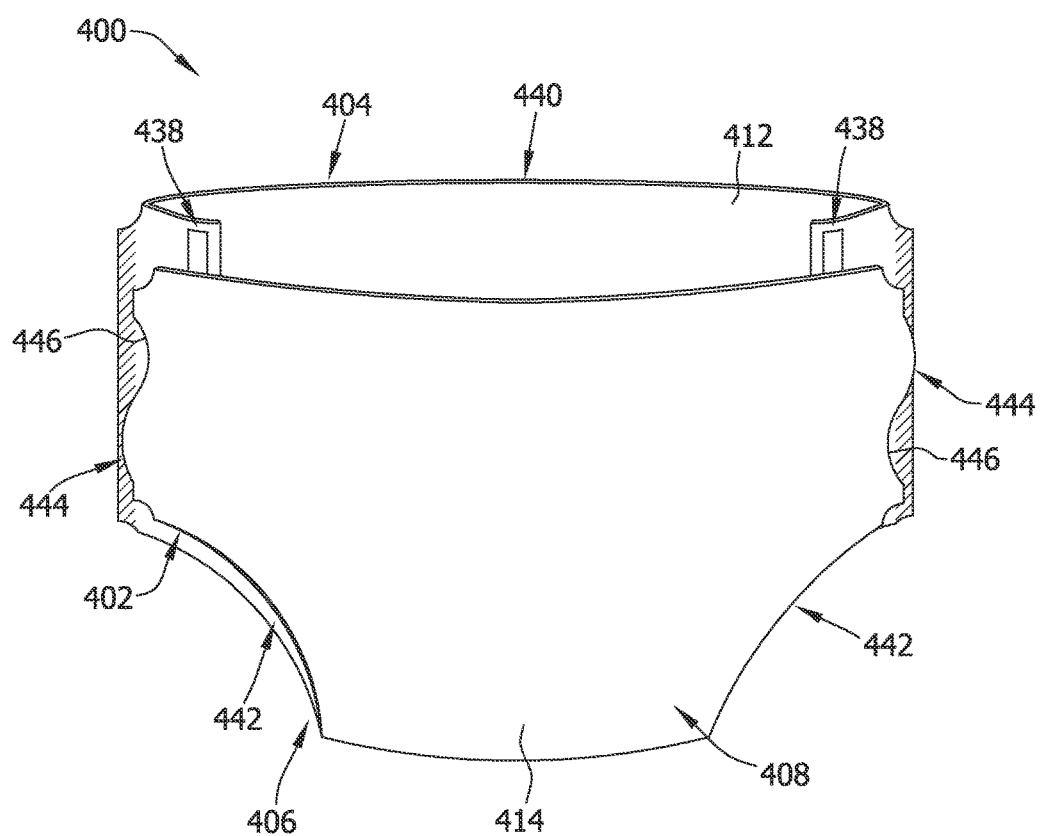
FIG. 9 is a front view of the diaper pant in a wear configuration.

FIG. 8 is a top plan view of another suitable embodiment of an absorbent article shown in the form of a diaper pant, indicated generally at 400. FIG. 9 is a front view of the diaper pant 400 in a wear configuration. Unless otherwise noted, the diaper pant 400 illustrated in FIGS. 8 and 9 is substantially identical to the diaper pant 10 illustrated and described above with respect to FIGS. 1 and 2.

As shown in FIG. 8, the diaper pant 400 includes a front region 402, a rear region 404, and a crotch region 406 extending between and interconnecting the front region 402 and the rear region 404. In the embodiment illustrated in FIG. 8, the front region 402, the rear region 404, and the crotch region 406 are formed from a single, continuous backsheet or chassis 408. The chassis 408 includes a front portion 410, a rear portion 412, and a longitudinally extending central portion 414 extending between and interconnecting the front portion 410 and the rear portion 412. The front portion 410 defines a front waist edge 416 and transversely opposed first and second front side edges 418, 420. The rear portion 412 defines a rear waist edge 422 and transversely opposed first and second rear side edges 424, 426.

An absorbent assembly 428 is attached to the chassis 408 along at least the central portion 414 using suitable attachment means including, but not limited to, adhesives, ultrasonic bonds, thermal bonds, pressure bonds, and combinations thereof. The absorbent assembly 428 is substantially identical to the absorbent assembly 34 described above with reference to FIGS. 1 and 2, including an outer cover 430, a bodyside liner 432, and an absorbent structure 434 disposed between the bodyside liner 432 and the absorbent structure 434. A portion of the bodyside liner 432 is shown cut away in FIG. 8 to reveal the underlying absorbent structure 434 and outer cover 430. In some embodiments, the outer cover 430 may be omitted from the absorbent assembly 428, and the absorbent structure 434 may be sandwiched between the bodyside liner 432 and the chassis 408.

The diaper pant 400 illustrated in FIGS. 8 and 9 also includes a fastening system 436. The fastening system 436 is substantially identical to the fastening system 60 described above with reference to FIGS. 1 and 2, including a pair of first fastener assemblies 62 disposed on the rear portion 412 of the chassis 408 and a pair of second fastener assemblies 64 disposed on the front portion 410 of the chassis 408.

As shown in FIG. 9, the front region 402 of the diaper pant 400 is joined to the rear region 404 via a pair of refastenable seams 438 to define a pull-on, pant-like configuration of the diaper pant 400 having a waist opening, indicated at 440, and two leg openings, indicated at 442. More specifically, the front portion 410 of the chassis 408 and the rear portion 412 of the chassis 408 are releasably attached to one another by the fastening system 436. In other suitable embodiments, the front region 402 of the diaper pant 400 can be joined to the rear region 404 via a pair of nonrefastenable side seams in a manner similar to the diaper pant 10 shown and described above with reference to FIG. 4.

The diaper pant 400 illustrated in FIGS. 8 and 9 also includes a pair of integrally formed finger tabs 444. The finger tabs 444 have substantially the same configuration and function in substantially the same manner as the finger tabs 66 described above with reference to FIGS. 1 and 2. The finger tabs 444 extend transversely outward from the front portion 410 of the chassis 408 along the first and second front side edges 418, 420, and are suitably sized and shaped to permit a user to grasp the finger tabs 444 and apply a peeling or tearing force thereto. Each finger tab 444 is partially defined by a cutout 446 that extends transversely inward into the front portion 410 along one of the first and second front side edges 418, 420. Each cutout 446 is shaped complementary to the corresponding finger tab 444 partially defined by the cutout 446. Further, each cutout 446 is shaped complementary to the finger tab 444 disposed on the opposite side edge of the front portion 410 from the cutout 446.

As shown in FIGS. 8 and 9, the finger tab 444 disposed on the first front side edge 418 is longitudinally offset (i.e., in the longitudinal direction of the diaper pant 400) from the finger tab 444 disposed on the second front side edge 420. Further, the finger tab 444 disposed on the first front side edge 418 is laterally aligned (i.e., in the lateral direction of the diaper pant 400) with the cutout 446 disposed on the second front side edge 420, and the finger tab 444 disposed on the second front side edge 420 is laterally aligned with the cutout 446 disposed on the first front side edge 418. As shown in FIGS. 8 and 9, the finger tabs 444 and the cutouts 446 give the first and second front side edges 418, 420 an oscillating or undulating appearance.

In other suitable embodiments, the finger tab 444 on one side of the front portion 410 may be other than laterally aligned with the cutout 446 on the opposite side edge of the front portion 410, and/or the finger tab 444 on one side edge of the front portion 410 may be other than longitudinally offset from the finger tab 444 on the other side edge of the front portion 410.

As noted above, the front region 402, the rear region 404, and the crotch region 406 of the diaper pant 400 are constructed from a single, continuous backsheet or chassis 408. The chassis 408 may be constructed from a variety of suitable materials, including liquid permeable materials and liquid impermeable materials. Suitable materials include, but are not limited to, single layer nonwovens, such as spunbond webs, or nonwoven laminates, such as spunbond laminates (e.g., spunbond/spunbond/spunbond (SSS)) and spunbond/meltblown laminates (e.g., spunbond/meltblown/spunbond (SMS)). The chassis 408 may be treated to impart a desired level of liquid permeability or impermeability to the chassis 408. In embodiments where the outer cover 430 is omitted from absorbent assembly 428, the chassis 408 is suitably constructed from a liquid impermeable material, and may generally be constructed from the same materials as the outer cover 42 described above with reference to FIGS. 1 and 2. In embodiments where the absorbent assembly 428 includes a liquid impermeable outer cover 430, chassis 408 may be constructed from liquid permeable materials and liquid impermeable materials, or only liquid permeable materials.

The chassis 408 may also be formed from a breathable or a non-breathable material. In some embodiments, the chassis 408 is formed from a breathable material, or a material that is treated or processed to be breathable. Other suitable materials from which the chassis 408 can be formed include woven and non-woven materials formed from natural or synthetic fibers; polyolefins, such as polypropylene or polyethylene; thermoplastic films; as well as other materials known to those skilled in the art.

In the illustrated embodiment, the chassis 408 is formed from a single continuous sheet or laminate that extends from the front waist edge 416 to the rear waist edge 422, and from the first front and rear side edges 418, 424 to the second front and rear side edges 420, 426.

Figure 10:
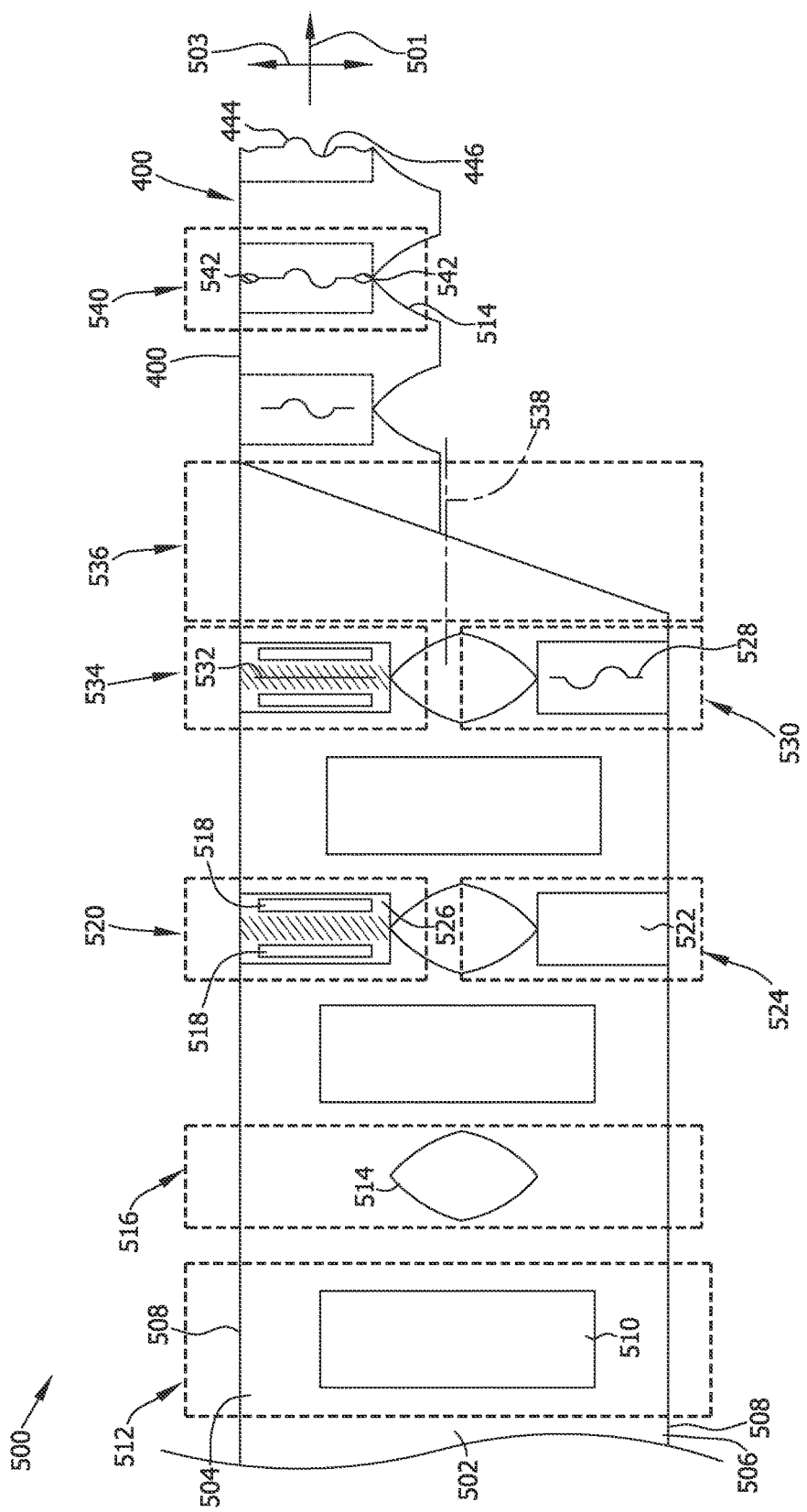
FIG. 10 is a schematic illustrating one suitable method of manufacturing the diaper pant of FIGS. 9 and 10.

FIG. 10 schematically illustrates one suitable method 500 of manufacturing the diaper pant 400 shown in FIGS. 8 and 9.

The method 500 includes feeding a web 502 of material in a machine direction 501. The web 502 defines a first portion 504 and a second portion 506 spaced from the first portion 504 in a cross-machine direction 503. The web 502 also includes laterally opposing side edges 508 extending in the machine direction 501. The web 502 is fed from a supply source (not shown) using any suitable apparatus, including, but not limited to, nip rolls, tensioning rolls, and combinations thereof.

The web 502 of material forms the chassis 408 of the diaper pant 400 (FIGS. 8 and 9). Thus, the web 502 may be constructed from the same materials as the chassis 408 (FIGS. 8 and 9) described above. In the embodiment illustrated in FIG. 10, the first portion 504 of the web 502 defines the rear portion 412 of the chassis 408 of the diaper pant 400 (FIGS. 8 and 9), and the second portion 506 defines the front portion 410 of the chassis 408 (FIGS. 8 and 9). In other suitable embodiments, the first portion 504 of the web 502 may define the front portion 410 of the chassis 408, and the second portion 506 may define the rear portion 412 of the chassis 408.

The method 500 further includes attaching an absorbent assembly 510 to the web 502 at an absorbent assembly attachment station 512. The absorbent assembly 510 is attached to the web 502 such that the absorbent assembly 510 is oriented in the cross-machine direction 503. The absorbent assembly 510 may have the same construction and comprise the same materials as the absorbent assemblies 34, 428 described above with reference to FIGS. 1 and 2 and FIGS. 8 and 9. The absorbent assembly 510 may be attached to the web 502 using any suitable attachment methods, such as those described above with reference to FIG. 5.

As shown in FIG. 10, the method 500 further includes forming leg cutouts 514 in the web 502 at a leg cutout station 516. The leg cutouts 514 are formed in the web 502 between the first portion 504 and the second portion 506, and define the leg openings 442 (FIG. 9) of the diaper pant 400 when the diaper pant 400 is formed. The leg cutout station 416 may include any suitable apparatus for forming leg cutouts 514 including, but not limited to, knife rolls, anvil rolls, die cutters, and combinations thereof.

The method 500 further includes attaching a first fastening component 518 to the first portion 504 of the web 502 at a first fastening component attachment station 520, and attaching a second fastening component 522 to the second portion 506 of the web 502 at a second fastening component attachment station 524. The first fastening component 518 and the second fastening component 522 may be attached to the web 502 in substantially the same manner as the first fastening component 116 and the second fastening component 120 described above with reference to FIG. 5. In some embodiments, for example, attaching the first fastening component 518 to the first portion 504 of the web 502 includes attaching a carrier sheet 526 to the first portion 504 of the web 502, and attaching the first fastening component 518 to the carrier sheet 526. The fastening component attachment stations 520, 524 may include any suitable apparatus to attach the first fastening component 518 to the first portion 504 of the web 502 and the second fastening component 522 to the second portion 506 of the web 502, including, but not limited to, adhesive applicators, compression rolls, nip rolls, laminator rolls, chill rolls, ultrasonic horns, anvils, and combinations thereof.

The method 500 further includes forming a partial cut line 528 through the second portion 506 of the web 502 at a first cutting station 530. The partial cut line 528 may be formed in substantially the same manner as the partial cut line 132 described above with reference to FIG. 5. The first cutting station 530 may include any suitable apparatus to form the partial cut line 528 in the second portion 506 of the web 502, including, but not limited to, knife rolls and anvil rolls. As shown in FIG. 10, the partial cut line 528 defines a finger tab 444 and a cutout 446 on the diaper pant 400 when the diaper pant 400 is formed. More specifically, the partial cut line 528 defines a finger tab 444 and a cutout 446 on two separate diaper pants 10—i.e., a leading diaper pant and a trailing diaper pant. In other suitable embodiments, the partial cut line 528 may define a finger tab 444 and/or a cutout 446 on only one diaper pant.

As shown in FIG. 10, the method 500 also includes forming a cut line 532 through the first portion 504 of the web 502 at a second cutting station 534. As shown in FIG. 10, the cut line 532 is a partial cut line. The cut line 532 may be formed in substantially the same manner as the cut line 146 described above with reference to FIG. 5. The second cutting station 534 may include any suitable apparatus to form the cut line 532 in the first portion 504 of the web 502, including, but not limited to, knife rolls and anvil rolls.

As shown in FIG. 10, the method 500 further includes folding the first portion 504 of the web 502 into face-to-face relationship with the second portion 506 of the web 502 at a folding station 536 after forming the partial cut line 528 and the cut line 532. Folding the first portion 504 of the web 502 into face-to-face relationship with the second portion 506 of the web 502 at the folding station 536 causes the first fastening components 518 to be releasably fastened to the second fastening components 522, thereby providing a prefastened diaper pant 400. Further, when the first portion 504 of the web 502 is folded into face-to-face relationship with the second portion 506 of the web 502, the partial cut line 528 in the second portion 506 of the web 502 is substantially aligned with the cut line 532 in the first portion 504 of the web 502.

Folding the first portion 504 of the web 502 into face-to-face relationship with the second portion 506 of the web 502 includes rotating one of the first portion 504 of the web 502 and the second portion 506 of the web 502 about a fold line 538 extending parallel to the machine direction 501. The folding station 536 may include any suitable folding mechanism to fold the first portion 504 of the web 502 in to face-to-face relationship with the second portion 506 of the web 502.

The method 500 further includes cutting the web 502 at a third cutting station 540 while the first portion 504 of the web 502 is positioned in face-to-face relationship with the second portion 506 of the web 502 to separate the diaper pant 10 from the web 502 and, in the illustrated embodiment, separate a leading diaper pant 400 from a trailing diaper pant 400. The third cutting station 540 may include any suitable apparatus to cut the first web 502, including, but not limited to, knife rolls and anvil rolls.

In the illustrated embodiment, cutting the web 502 at the third cutting station 540 includes forming cutouts 542 along the laterally opposing side edges 508 of the web 502. The cutouts 542 intersect the partial cut line 528 formed in the second portion 506 of the web 502, and the cut line 532 formed in the first portion 504 of the web 502, thereby forming a continuous cut line that extends across each of the first portion 504 of the web 502 and the second portion 506 of the web 502. Further, as shown in FIG. 10, one of the cutouts 542 adjoins the leg cutouts 514 formed in the web 502. In other suitable embodiments, cutting the web 502 may include forming a cutout 542 along only one of the side edges 508 of the web 502. In yet other suitable embodiments, cutting the web 502 may include forming one or more linear cut lines that intersect the partial cut line 528 and the cut line 532 to form continuous cut lines that extend across each of the first portion 504 of the web 502 and the second portion 506 of the web 502.

The method 500 illustrated in FIG. 10 provides a diaper pant 400 having a single, continuous chassis 408 with integrally formed finger tabs 444 that facilitate separating the refastenable seams 438 of the diaper pant 400 (shown in FIGS. 8 and 9) when a user desires to remove the diaper pant 400. Forming a partial cut line 528 in the second web 502, as opposed to a full cut line, enables the finger tabs 444 to be selectively formed on only one of the front portion 410 of the chassis 408 and the rear portion 412 of the chassis 408. The methods illustrated and described above with reference to FIGS. 6 and 7 may also be carried out using a single web to provide a diaper pant having a single, continuous chassis with integrally formed finger tabs on the front portion and the rear portion of the chassis, and a diaper pant having the front and rear portions of a single, continuous chassis joined by nonrefastenable side seams.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of manufacturing an absorbent article, the method comprising:
    feeding a first web of material in a machine direction;
    feeding a second web of material in the machine direction, the second web being spaced from the first web by a gap;
    attaching an absorbent assembly to the first web and the second web such that the absorbent assembly spans the gap between the first and second webs;
    forming a partial cut line through the second web, wherein the second web includes opposing side edges extending in the machine direction, the partial cut line spaced from the side edges of the second web;
    folding the first web into face-to-face relationship with the second web after forming the partial cut line; and
    cutting the first and second webs after folding the first web into face-to-face relationship with the second web to separate the absorbent article from the first and second webs, the partial cut line defining at least one finger tab on the absorbent article.

2. The method as set forth in claim 1 further comprising:
    attaching a first fastening component to the first web; and
    attaching a second fastening component to the second web, the second fastening component configured for releasable attachment with the first fastening component.

3. The method as set forth in claim 2, wherein forming the partial cut line comprises forming the partial cut line through one of the first fastening component and the second fastening component.

4. The method as set forth in claim 2 further comprising attaching a carrier sheet to the first web, wherein attaching the first fastening component to the first web comprises attaching the first fastening component to the carrier sheet.

5. The method as set forth in claim 4, wherein the carrier sheet includes a leading edge and a trailing edge, wherein attaching the carrier sheet comprises bonding the carrier sheet to the first web along a bond zone such that the leading edge and the trailing edge are free edges, wherein attaching the first fastening component to the first web includes attaching the first fastening component to the carrier sheet between the bond zone and one of the free edges.

6. The method as set forth in claim 1, wherein the partial cut line defines a cutout in the absorbent article adjacent to the at least one finger tab.

7. The method as set forth in claim 1, wherein cutting the first and second webs separates a leading absorbent article from a trailing absorbent article, the partial cut line defining at least one finger tab on each of the leading absorbent article and the trailing absorbent article.

8. The method as set forth in claim 1, wherein each of the first web and the second web include laterally opposing side edges extending in the machine direction, wherein cutting the first and second webs comprises forming a cutout along at least one of the side edges of the second web while the first and second webs are in face-to-face relationship, the cutout intersecting the partial cut line in the second web.

9. The method as set forth in claim 1, wherein the absorbent article includes a front panel and a rear panel interconnected by the absorbent assembly, the first web defining one of the front panel and the rear panel, and the second web defining the other of the front panel and the rear panel.

10. An absorbent article defining a longitudinal direction and a transverse direction, the absorbent article comprising:
    a front panel defining a front waist edge and first and second front side edges spaced apart in the transverse direction;
    a rear panel defining a rear waist edge spaced apart from the first waist edge in the longitudinal direction, and first and second rear side edges spaced apart in the transverse direction, the front panel being connected to the rear panel by a pair of side seams when the absorbent article is in a wear configuration to define a waist opening and a pair of leg openings, each side seam extending between one of the leg openings and the waist opening;

an absorbent assembly extending longitudinally between and interconnecting the front panel and the rear panel; and a gripping feature comprising a pair of finger tabs and a pair of cutouts, the pair of finger tabs integrally formed with one of the front panel and the rear panel, the pair of finger tabs including a first finger tab extending transversely outward from the first side edge of the corresponding front panel or rear panel, and a second finger tab extending transversely outward from the second side edge of the corresponding front panel or rear panel, the pair of cutouts formed in one of the front panel and the rear panel, the pair of cutouts including a first cutout extending transversely inward from the first side edge of the corresponding front panel or rear panel, and a second cutout extending transversely inward from the second side edge of the corresponding front panel or rear panel, wherein the first and second finger tabs are offset from one another in the longitudinal direction.

11. The absorbent article as set forth in claim 10, wherein the gripping feature is a seam separating feature configured to facilitate manual separation of the side seams.

12. The absorbent article as set forth in claim 10, wherein the first finger tab is partially defined by a first cutout extending transversely inward into the front panel or rear panel, and the second finger tab is partially defined by a second cutout extending transversely inward into the front panel or rear panel, the first finger tab being laterally aligned with the second cutout, and the second finger tab being laterally aligned with the first cutout.

13. The absorbent article as set forth in claim 12, wherein the first cutout is shaped complementary to the second finger tab and the second cutout is shaped complementary to the first finger tab.

14. The absorbent article as set forth in claim 10, wherein the pair of finger tabs is a first pair of finger tabs and is integrally formed with the front panel, the gripping feature further comprising a second pair of finger tabs integrally formed with the rear panel, the second pair of finger tabs including a third finger tab extending transversely outward from the rear panel along the first side edge of the rear panel, and a fourth finger tab extending transversely outward from the rear panel along the second side edge of the rear panel.

15. The absorbent article as set forth in claim 10 further comprising a pair of first fastener assemblies disposed on one of the front panel and the rear panel, and a pair of second fastener assemblies disposed on the other of the front panel and the rear panel, each first fastener assembly configured to matingly engage one of the second fastener assemblies to form one side seam of the pair of side seams, wherein each fastener assembly from one of the pair of first fastener assemblies and the pair of second fastener assemblies comprises:

a carrier sheet having a fixed edge attached to one of the front panel and the rear panel adjacent one of the corresponding side edges of the front panel or rear panel, and a free edge spaced from the fixed edge in the transverse direction; and a fastening component attached to the carrier sheet proximate the free edge.

16. An absorbent article defining a longitudinal direction and a transverse direction, the absorbent article comprising:

a chassis including a front portion, a rear portion, and a crotch portion extending between and interconnecting the front portion and the rear portion, the front portion defining first and second front side edges spaced apart in the transverse direction, the rear portion defining first and second rear side edges spaced apart in the transverse direction, the front portion being connected to the rear portion by a pair of side seams when the absorbent article is in a wear configuration to define a waist opening and a pair of leg openings, each side seam extending between one of the leg openings and the waist opening;

an absorbent assembly attached to the chassis along at least the crotch portion; and a gripping feature comprising a pair of finger tabs and a pair of cutouts, the pair of finger tabs integrally formed with one of the front portion and the rear portion of the chassis, the pair of finger tabs including a first finger tab extending transversely outward from the first side edge of the corresponding front portion or rear portion, and a second finger tab extending transversely outward from the second side edge of the corresponding front portion or rear portion, the pair of cutouts formed in one of the front portion and the rear portion of the chassis, the pair of cutouts including a first cutout extending transversely inward from the first side edge of the corresponding front portion or rear portion, and a second cutout extending transversely inward from the second side edge of the corresponding front portion or rear portion, wherein the first and second finger tabs are offset from one another in the longitudinal direction.

17. The absorbent article as set forth in claim 16, wherein the gripping feature is a seam separating feature configured to facilitate manual separation of the side seams.

18. The absorbent article as set forth in claim 16, wherein the pair of finger tabs is a first pair of finger tabs and is integrally formed with the front portion of the chassis, the gripping feature further comprising a second pair of finger tabs integrally formed with the rear portion of the chassis, the second pair of finger tabs including a third finger tab extending transversely outward from the rear portion along the first side edge of the rear portion, and a fourth finger tab extending transversely outward from the rear portion along the second side edge of the rear portion.

19. The absorbent article as set forth in claim 16, further comprising a pair of first fastener assemblies disposed on one of the front portion and the rear portion of the chassis, and a pair of second fastener assemblies disposed on the other of the front portion and the rear portion of the chassis, each first fastener assembly configured to matingly engage one of the second fastener assemblies to form one side seam of the pair of side seams, wherein each fastener assembly from one of the pair of first fastener assemblies and the pair of second fastener assemblies comprises:

a carrier sheet having a fixed edge attached to one of the front portion and the rear portion of the chassis adjacent one of the corresponding side edges of the front portion or rear portion, and a free edge spaced from the fixed edge in the transverse direction; and a fastening component attached to the carrier sheet proximate the free edge.

20. The absorbent article as set forth in claim 16, wherein the first cutout formed in the first side edge is laterally aligned with the second finger tab on the second side edge, and the second cutout formed in the second side edge is laterally aligned with the first finger tab on the first side edge.

\* \* \* \* \*